(12) United States Patent
Abe et al.

(10) Patent No.: US 7,348,318 B2
(45) Date of Patent: Mar. 25, 2008

(54) α-AMINO-N-(DIAMINOPHOSPHINYL)LACTAM DERIVATIVES

(75) Inventors: Masatoshi Abe, Tokyo (JP); Masashi Nagai, Nishitokyo (JP); Keiichirou Yamamoto, Tokyo (JP); Chihiro Nishimura, Chiba (JP)

(73) Assignees: Nippon Kayaku Kabushiki Kaisha, Tokyo (JP); Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 617 days.

(21) Appl. No.: 10/508,573

(22) PCT Filed: Mar. 24, 2003

(86) PCT No.: PCT/JP03/03534

§ 371 (c)(1),
(2), (4) Date: Sep. 22, 2004

(87) PCT Pub. No.: WO03/080633

PCT Pub. Date: Oct. 2, 2003

(65) Prior Publication Data

US 2005/0164989 A1 Jul. 28, 2005

(30) Foreign Application Priority Data

Mar. 25, 2002 (JP) ............................. 2002-082581

(51) Int. Cl.
A61K 31/675 (2006.01)
A61K 31/45 (2006.01)
C07D 211/92 (2006.01)
C07F 9/06 (2006.01)

(52) U.S. Cl. .................... 514/89; 546/21; 548/412; 540/364; 540/527; 514/79; 514/91

(58) Field of Classification Search ................ 514/89, 514/91, 79; 546/21; 548/412; 540/364, 540/527
See application file for complete search history.

(56) References Cited

U.S. PATENT DOCUMENTS 6,214,340 B1   4/2001 Takeuchi et al. .......... 424/117

6,579,989 B1 * 6/2003 Takeuchi et al. ............ 548/412

FOREIGN PATENT DOCUMENTS

| EP | 1 184 388 | 3/2002 |
|---|---|---|
| JP | 54-12391 | 1/1979 |
| JP | 1-40036 | 8/1989 |
| JP | 2000-327689 | 11/2000 |
| WO | 94/03055 | 2/1994 |
| WO | 99/25719 | 5/1999 |

OTHER PUBLICATIONS

Immunol. Today, vol. 15, 180-184 (1994).
J.Clin. Invest, vol. 78, 906-913 (1994).
Diabetes, vol. 47, p. 1253 (1998).
J.Am. Chem. Soc., vol. 116, p. 10860 (1994).
J.Med. Chem., vol. 39, p. 2087 (1996).

* cited by examiner

Primary Examiner—Charanjit S. Aulakh
(74) Attorney, Agent, or Firm—Nields & Lemack

(57) ABSTRACT

There are disclosed a novel α-amino-N-(diaminophosphinyl)lactam derivative represented by general formula (1):

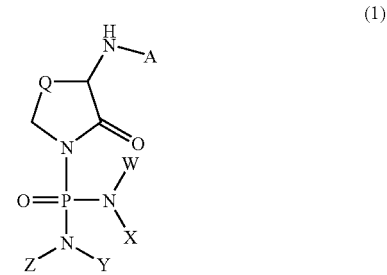

(1)

wherein, for example, A is a hydrogen atom or a substituent such as a lower alkyl group or the like; W, X, Y and Z are independently a hydrogen atom or a substituent such as a lower alkyl group, aryl group, arylacyl group, arylaminocarbonyl group or the like; and Q is $-(CH_2)_n-$ wherein n is 0 to 3, or its salt, and a therapeutic agent and a prophylactic agent for myelosuppression, a therapeutic agent for infectious diseases, an agent for increasing the number of leukocytes and a dipeptidyl peptidase IV inhibitor which comprise the above-mentioned derivative or salt thereof as an active ingredient.

17 Claims, No Drawings

α-AMINO-N-(DIAMINOPHOSPHINYL)LACTAM DERIVATIVES

TECHNICAL FIELD

The present invention relates to novel α-amino-N-(diaminophosphinyl)lactam derivatives, their salts, their hydrates or their solvates, and pharmaceutical compositions containing any of said compounds. The compounds of the present invention are expected to be useful as prophylactic or therapeutic agents for myelosuppression, prophylactic or therapeutic agents for infectious diseases and agents for increasing the number of leukocytes. Moreover, the compounds of the present invention have inhibitory effect on dipeptidyl peptidase IV and hence are expected to be useful as prophylactic or therapeutic agents for diseases in which dipeptidyl peptidase IV seems to participate, such as immunomodurators, hormone modulators, anti-HIV agents, antiallergics, anti-inflammatories, antirheumatics, therapeutic agents for type II diabetes, etc.

BACKGROUND ART

It is known that the suppression of the functions of bone marrow by various causes seriously worsens systemic condition to become dangerous to life. As morbidities due to such myelosuppressive conditions, hypoplastic anemia, thrombopenia, leukopenia and the like are known.

As the mechanism of the onset of leukopenia among them, the decrease of leukocyte production and the acceleration of leukocyte destruction are mentioned. Causes for the decrease of leukocyte production include congenital diseases, irradiation with radiation, hypoplastic anemia, administration of an antitumor agent or antibiotic, etc. On the other hand, causes for the acceleration of leukocyte destruction include infectious diseases, immunological abnormalities, etc.

As a therapeutic agent for leukopenia, granulocyte colony-stimulating factor (G-CSF) and macrophage colony-stimulating factor (M-CSF) are effective at present. On the other hand, erythropoietin is used as a therapeutic agent for erythropenia. The employment of interleukin-6, interleukin-11, thrombopoietin and the like as medicines is in progress for treating thrombopenia. In addition, the employment of granulocyte-macrophage colony-stimulating factor (GM-CSF) and the like as therapeutic agents for myelosuppression is in progress.

For example, compounds formed by the substitution of a sugar by a N-acyl-N-alkylamino group at the 1-position are known (JP-B-1-40036) as compounds having defensive effect on infectious diseases caused by bacteria, fungi, etc.

On the other hand, dipeptidyl peptidase IV is a serine protease that detaches the N-terminal dipeptide of a protein or peptide in which the second amino acid residue from the N-terminus is proline or alanine. In mammals, dipeptidyl peptidase IV is present in various organs such as liver, kidney, small intestine, hemocytes, etc. Although the biological role of dipeptidyl peptidase IV has not completely been established, it is considered that dipeptidyl peptidase IV participates in the metabolism of neuropeptides and hormones, the activation of T cells, the intrusion of HIV into lymph cells, and the like (see Immunol. Today, Vol. 15, 180-184 (1994) and J. Clin. Invest., Vol. 78, 906-913 (1994)). Therefore, dipeptidyl peptidase IV inhibitors are expected to be usable as hormone modulators, immunomodurators, anti-inflammatories, antiallergics, antirheumatics, anti-HIV agents, etc. In addition, it has recently been proved that glucagon-like peptide 1, which is an stimulating factor for insulin secretion in spleen, is inactivated by dipeptidyl peptidase IV. Therefore, the dipeptidyl peptidase IV inhibitors are promising also as therapeutic agents for type II diabetes (see Diabetes, VOl. 47, p. 1253 (1998)).

As a compound having both effect on hemocytes such as leukocytes and inhibitory effect on dipeptidyl peptidase IV, Val-boroPro is known which is a dipeptide containing boron (see International Publication No. 94/03055). However, it has been reported that such compounds having boron in the molecule are decreased in activity in a neutral buffer solution because an amine coordinates with the boron, an active center (see J. Am. Chem. Soc., Vol. 116, p. 10860 (1994)), and that they exhibit an insufficient preference for dipeptidyl peptidase IV over other enzymes (see J. Med. Chem., Vol. 39, p. 2087 (1996)). It is not easy to develop these compounds as medicines, and they are utterly different in skeleton from the compounds of the present invention. As compounds similar in skeleton to the compounds of the present invention, there are known sulphostin and compounds analogous thereto which have inhibitory effect on dipeptidyl peptidase IV (see International Publication No. 99/25719 and JP-A-2000-327689).

DISCLOSURE OF THE INVENTION

An object of the present invention is to provide novel α-amino-N-(diaminophosphinyl)lactam derivatives to be used as prophylactic or therapeutic agents for myelo-suppression, therapeutic agents for infectious diseases and agents for increasing the number of leukocytes. Another object of the present invention is to provide novel α-amino-N-(diaminophosphinyl)lactam derivatives having inhibitory effect on dipeptidyl peptidase IV, and pharmaceutical compositions containing any of these compounds as an active ingredient.

The present inventors earnestly investigated sulphostin derivatives and consequently found that novel α-amino-N-(diaminophosphinyl)lactam derivatives represented by general formula (1) and pharmacologically acceptable salts thereof have an effect of increasing the number of leukocytes and have no influence on the number of platelets. In detail, by using mice subjected to a myelosuppression model induced by an anticancer agent, it was confirmed that the novel α-amino-N-(diaminophosphinyl)lactam derivatives represented by general formula (1) and pharmacologically acceptable salts thereof have an effect of alleviating and treating leukopenia. In addition, by using normal mice, it was confirmed that the derivatives and salts have an effect of increasing the number of leukocytes and have no influence on the number of platelets. On the basis of these facts, it was found that the compounds of the present invention can be used as the active ingredient of a prophylactic agent and a therapeutic agent for myelosuppressive diseases, an agent for increasing the number of leukocytes and a therapeutic agent for infectious diseases, and that the usefulness of the compounds is greater because they have no influence on platelet at all. Furthermore, the present inventors also found that the novel α-amino-N-(diaminophosphinyl)lactam derivatives represented by general formula (1) and pharmacologically acceptable salts thereof have inhibitory effect on dipeptidyl peptidase IV, whereby the present invention has been accomplished.

That is, the present invention relates to the following items (1) to (22).

(1) An α-amino-N-(diaminophosphinyl)lactam derivative represented by the following general formula (1), or a pharmacologically acceptable salt thereof:

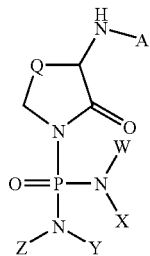

wherein A is a hydrogen atom, a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, an arylamino group, a heteroarylamino group, a lower acylamino group, a carboxyl group, a lower alkoxycarbonyl group, a carbamoyl group or a lower alkylaminocarbonyl group; W, X, Y and Z are independently a hydrogen atom, a lower alkyl group, an aryl group, a heteroaryl group, a lower alkenyl group, a cycloalkyl group, a lower acyl group, an arylacyl group, a heteroarylacyl group, a lower alkylaminocarbonyl group or an arylaminocarbonyl group, each of these groups being able to be substituted by a lower alkyl group, an aryl group, a heteroaryl group, a lower alkoxy group, an aryloxy group, a hydroxyl group, an amino group, a lower alkylamino group, a di-lower alkylamino group, a lower acylamino group, a carboxyl group, a lower alkoxycarbonyl group, a halogen atom, a cyano group, a nitro group, a carbamoyl group or a lower alkylaminocarbonyl group, or one or both of a combination of W and X and a combination of Y and Z form a cyclic group (s) through a saturated or unsaturated carbon-carbon bond or a saturated or unsaturated carbon-carbon bond containing 1 to 3 heteroatoms selected from nitrogen atom, oxygen atom and sulfur atom, said cyclic group (s) being able to be unsubstituted or substituted by a substituent (s) selected from the group consisting of lower alkyl groups, aryl groups, heteroaryl groups, halogen atoms, nitro group, cyano group, lower alkoxycarbonyl groups, carbamoyl group, lower alkylaminocarbonyl groups and carboxyl group, and W and X, or Y and Z, which do not form a ring, have the above-mentioned substituent; and Q is —(CH$_2$)$_n$— wherein n is 0 to 3.

(2) An α-amino-N-(diaminophosphinyl)lactam derivative or a pharmacologically acceptable salt thereof according to the item (1), wherein in general formula (1), A is a hydrogen atom or a lower alkyl group, said lower alkyl group being able to be substituted by an aryl group or a heteroaryl group.

(3) An α-amino-N-(diaminophosphinyl)lactam derivative or a pharmacologically acceptable salt thereof according to the item (1), wherein in general formula (1), A is a hydrogen atom; W, X, Y and Z are independently a hydrogen atom, a lower alkyl group, an aryl group, a lower acyl group, an arylacyl group, a lower alkylaminocarbonyl group or an arylaminocarbonyl group, each of these groups being able to be substituted by a lower alkyl group, an aryl group, a lower alkoxy group, an aryloxy group, a carboxyl group, a halogen atom, a cyano group, a nitro group, a carbamoyl group or a lower alkylaminocarbonyl group; and Q is —(CH$_2$)$_n$— wherein n is 0 to 3.

(4) An α-amino-N-(diaminophosphinyl)lactam derivative or a pharmacologically acceptable salt thereof according to the item (1), wherein in general formula (1), A is a hydrogen atom; W, X, Y and Z are independently a hydrogen atom, a lower alkyl group, a phenyl group, a 4-methoxyphenyl group, an acetyl group, a butanoyl group, a phenylacetyl group, a 3-phenylpropanoyl group, a phenoxyacetyl group, a t-butylacetyl group, a cyclohexanecarbonyl group, a cinnamoyl group, a benzoyl group, a 4-methoxybenzoyl group, a 4-nitrobenzoyl group, a 4-fluorobenzoyl group, a thenoyl group, an ethylaminocarbonyl group or a phenylaminocarbonyl group; and Q is —(CH$_2$)$_n$— wherein n is 0 to 3.

(5) An α-amino-N-(diaminophosphinyl)lactam derivative or a pharmacologically acceptable salt thereof according to the item (1), wherein in general formula (1), A is a hydrogen atom; W, X, Y and Z are independently a hydrogen atom, a lower alkyl group, a phenyl group, a 4-methoxyphenyl group, an acetyl group, a butanoyl group, a phenylacetyl group, a 3-phenylpropanoyl group, a phenoxyacetyl group, a t-butylacetyl group, a cyclohexanecarbonyl group, a cinnamoyl group, a benzoyl group, a 4-methoxybenzoyl group, a 4-nitrobenzoyl group, a 4-fluorobenzoyl group, a thenoyl group, an ethylaminocarbonyl group or a phenylaminocarbonyl group; and Q is —(CH$_2$)$_2$— (an ethylene group).

(6) An α-amino-N-(diaminophosphinyl)lactam derivative or a pharmacologically acceptable salt thereof according to the item (1), wherein in general formula (1), A is a hydrogen atom; all of W, X, Y and Z are hydrogen atoms; and Q is —(CH$_2$)$_n$— wherein n is 0 to 3.

(7) An α-amino-N-(diaminophosphinyl)lactam derivative or a pharmacologically acceptable salt thereof according to the item (1), wherein in general formula (1), A is a hydrogen atom; all of W, X, Y and Z are hydrogen atoms; and Q is —(CH$_2$)$_2$— (an ethylene group)

(8) An α-amino-N-(diaminophosphinyl)lactam derivative or a pharmacologically acceptable salt thereof according to the item (1), wherein in general formula (1), A is a hydrogen atom; all of W, X, Y and Z are hydrogen atoms; and Q is —CH$_2$— (a methylene group).

(9) An α-amino-N-(diaminophosphinyl)lactam derivative or a pharmacologically acceptable salt thereof according to the item (1), wherein in general formula (1), A is a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, a lower acylamino group, a carboxyl group, a carbamoyl group, a lower alkoxycarbonyl group or a lower alkylaminocarbonyl group; W, X, Y and Z are independently a hydrogen atom, a lower alkyl group, an aryl group, a cycloalkyl group, a lower acyl group, an arylacyl group, a heteroarylacyl group, a lower alkylaminocarbonyl group or an arylaminocarbonyl group, each of these groups being able to be substituted by a lower alkyl group, an aryl group, a heteroaryl group, a lower alkoxy group, an aryloxy group, a carboxyl group, a halogen atom, a cyano group, a nitro group, a carbamoyl group or a lower alkylaminocarbonyl group; and Q is —(CH$_2$)$_n$— wherein n is 0 to 3.

(10) An α-amino-N-(diaminophosphinyl)lactam derivative or a pharmacologically acceptable salt thereof according to the item (1), wherein in general formula (1), A is a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, a lower acylamino group, a carboxyl group, a carbamoyl group, a lower alkoxycarbonyl group or a lower alkylaminocarbonyl group; all of W, X, Y and Z are hydrogen atoms; and Q is —(CH$_2$)$_n$— wherein n is 0 to 3.

(11) An α-amino-N-(diaminophosphinyl)lactam derivative or a pharmacologically acceptable salt thereof according to the item (1), wherein in general formula (1), A is a lower alkyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a lower acylamino group, a carboxyl group, a carbamoyl group, a lower alkoxycarbonyl group or a lower alkylaminocarbonyl group; all of W, X, Y and Z are hydrogen atoms; and Q is —(CH$_2$)$_n$— wherein n is 0 to 3.

(12) An α-amino-N-(diaminophosphinyl)lactam derivative or a pharmacologically acceptable salt thereof according to the item (1), wherein in general formula (1), A is a lower alkyl group or a cycloalkyl group, each of these groups being able to be substituted by an aryl group or a heteroaryl group; all of W, X, Y and Z are hydrogen atoms; and Q is —(CH$_2$)$_n$— wherein n is 0 to 3.

(13) An α-amino-N-(diaminophosphinyl)lactam derivative or a pharmacologically acceptable salt thereof according to the item (1), wherein in general formula (1), A is a methyl, ethyl, n-propyl, isopropyl or n-butyl group which may be substituted by a phenyl group or a 2-furyl group; all of W, X, Y and Z are hydrogen atoms; and Q is —(CH$_2$)$_n$— wherein n is 0 to 3.

(14) An α-amino-N-(diaminophosphinyl)lactam derivative or a pharmacologically acceptable salt thereof according to the item (1), wherein in general formula (1), A is a methyl, ethyl, n-propyl, isopropyl or n-butyl group which may be substituted by a phenyl group or a 2-furyl group; all of W, X, Y and Z are hydrogen atoms; and Q is —(CH$_2$)$_n$— wherein n is 1 or 2.

(15) A drug for mammal or a pharmaceutical composition for prophylaxis or treatment of diseases, which comprises a compound or a pharmacologically acceptable salt thereof according to any one of the above items (1) to (14) as an active ingredient.

(16) A pharmaceutical composition for prophylaxis or treatment of myelosuppressive diseases comprising a compound or a pharmacologically acceptable salt thereof according to any one of the above items (1) to (14) as an active ingredient.

(17) A pharmaceutical composition for prophylaxis or treatment of leukopenia comprising a compound or a pharmacologically acceptable salt thereof according to any one of the above items (1) to (14) as an active ingredient.

(18) A pharmaceutical composition for prophylaxis or treatment of infectious diseases comprising a compound or a pharmacologically acceptable salt thereof according to any one of the above items (1) to (14) as an active ingredient.

(19) A pharmaceutical composition for increasing the number of leukocytes comprising a compound or a pharmacologically acceptable salt thereof according to any one of the above items (1) to (14) as an active ingredient.

(20) A dipeptidyl peptidase IV inhibitor comprising a compound or a pharmacologically acceptable salt thereof according to any one of the above items (1) to (14) as an active ingredient.

(21) An immunomodurator, a hormone modulator, an anti-inflammatory, an anti-HIV agent, an antiallergic or a pharmaceutical composition for prophylaxis or treatment of rheumatism, which comprises a compound or a pharmacologically acceptable salt thereof according to any one of the above items (1) to (14) as an active ingredient.

(22) A pharmaceutical composition for prophylaxis or treatment of type II diabetes comprising a compound or a pharmacologically acceptable salt thereof according to any one of the above items (1) to (14) as an active ingredient.

BEST MODE FOR CARRYING OUT THE INVENTION

In the present invention, the term "lower alkyl group" means a straight chain or branched chain alkyl group of 1 to 6 carbon atoms. The lower alkyl group includes, for example, methyl group, ethyl group, n-propyl group, isopropyl group, n-butyl group, sec-butyl group, tert-butyl group, n-pentyl group and n-hexyl group. Of these, methyl group, ethyl group, n-propyl group, isopropyl group and n-butyl group can be mentioned as preferable groups.

In the present invention, the term "aryl group" means an aromatic hydrocarbon group of 6 to 14 carbon atoms. The aryl group includes, for example, phenyl group, biphenyl group, naphthyl group, anthryl group and phenanthryl group. Of these, phenyl group can be mentioned as a preferable group.

In the present invention, the term "heteroaryl group" means a 5- to 7-membered heteroaromatic ring containing 1 to 3 heteroatoms which may be the same or different and are selected from nitrogen atom, oxygen atom and sulfur atom. The heteroaryl group includes, for example, furyl group, thienyl group, imidazolyl group, oxazolyl group, thiazolyl group, pyridyl group, indolyl group, pyrimidinyl group and pyridazinyl group. Of these, pyridyl group and furyl group can be mentioned as preferable groups.

In the present invention, the term "lower alkoxy group" means a lower alkyloxy group. As described above, the term "lower alkyl group" means a straight chain or branched chain alkyl group of 1 to 6 carbon atoms. The lower alkoxy group includes, for example, methoxy group, ethoxy group, n-propoxy group, isopropoxy group, n-butoxy group, isobutoxy group and tert-butoxy group. Of these, methoxy group and ethoxy group can be mentioned as preferable groups.

In the present invention, the term "aryl" in the term "aryloxy group" means an aromatic hydrocarbon group of 6 to 14 carbon atoms as described above. The aryloxy group includes, for example, phenoxy group and naphthoxy group. Of these, phenoxy group can be mentioned as a preferable group.

In the present invention, the term "lower alkenyl group" means a straight chain or branched chain alkenyl group of 2 to 6 carbon atoms. The lower alkenyl group includes, for example, vinyl group, allyl group, isopropenyl group and 3-butenyl group.

In the present invention, the term "cycloalkyl group" means a saturated cyclic hydrocarbon group of 3 to 8 carbon atoms. The cycloalkyl group includes, for example, cyclopropyl group, cyclobutyl group, cyclopentyl group, cyclohexyl group, cycloheptyl group and cyclooctyl group. Of these, cyclopentyl group and cyclohexyl group can be mentioned as preferable groups.

In the present invention, the term "halogen atom" means a fluorine atom, a chlorine atom, a bromine atom or an iodine atom. Of these, fluorine atom and chlorine atom can be mentioned as preferable atoms.

In the present invention, the term "lower acyl group" means a lower alkylcarbonyl group, a lower alkenylcarbonyl group or a lower cycloalkylcarbonyl group, and further means a group formed by bonding of carbonyl to the above-mentioned lower alkyl, lower alkenyl or lower cycloalkyl. The lower acyl group includes, for example, acetyl group, propanoyl group, butanoyl group, pentanoyl group, acryloyl group, crotonyl group, cyclopropanecarbonyl group, cyclobutanecarbonyl group, cyclopentanecarbonyl group, cyclohexanecarbonyl group and cycloheptanecarbonyl group. Of these, acetyl group, propanoyl group, butanoyl group, acryloyl group, cyclopentanecarbonyl group and cyclohexanecarbonyl group can be mentioned as preferable groups.

In the present invention, the term "lower alkylamino group" means a group formed by bonding of the above-mentioned lower alkyl group to an amino group. The lower alkylamino group includes, for example, methylamino group, ethylamino group, n-propylamino group, isopropylamino group, n-butylamino group and n-hexylamino group. Of these, methylamino group, ethylamino group and n-propylamino group can be mentioned as preferable groups.

In the present invention, the term "di-lower alkylamino group" means a group formed by bonding of two of the above-mentioned lower alkyl groups to an amino group. The di-lower alkylamino group includes, for example, dimethylamino group, diethylamino group and di-n-propylamino group. Of these, dimethylamino group and diethylamino group can be mentioned as preferable groups.

In the present invention, the term "lower acylamino group" means a group formed by bonding of the above-mentioned lower acyl group to an amino group. The lower acylamino group includes, for example, acetylamino group, propanoylamino group, butanoylamino group and pentanoylamino group. Of these, acetylamino group can be mentioned as a preferable group.

In the present invention, the term "lower alkoxycarbonyl group" means a group formed by bonding of carbonyl to the above-mentioned lower alkoxy group. The lower alkoxycarbonyl group includes, for example, methoxycarbonyl group, ethoxycarbonyl group, n-propoxycarbonyl group, isopropoxycarbonyl group, n-butoxycarbonyl group, isobutoxycarbonyl group and tert-butoxycarbonyl group. Of these, methoxycarbonyl group and ethoxycarbonyl group can be mentioned as preferable groups.

In the present invention, the term "lower alkylaminocarbonyl group" means a group formed by bonding of carbonyl to the above-mentioned lower alkylamino group. The lower alkylaminocarbonyl group includes, for example, methylaminocarbonyl group, ethylaminocarbonyl group, n-propylaminocarbonyl group, isopropylaminocarbonyl group, n-butylaminocarbonyl group and n-hexylaminocarbonyl group. Of these, methylaminocarbonyl group, ethylaminocarbonyl group and n-propylaminocarbonyl group can be mentioned as preferable groups.

In the present invention, the term "arylacyl group" means a group formed by bonding of the above-mentioned aryl group to an acyl group. The arylacyl group includes, for example, benzoyl group and naphthoyl group. Of these, benzoyl group can be mentioned as a preferable group.

In the present invention, the term "heteroarylacyl group" means a group formed by bonding of the above-mentioned heteroaryl group to an acyl group. The heteroarylacyl group includes, for example, thenoyl group, furoyl group and nicotinoyl group. Of these, thenoyl group can be mentioned as a preferable group.

In the present invention, the term "arylamino group" means a group formed by bonding of an amino group to the above-mentioned aryl group. The arylamino group includes, for example, phenylamino group, biphenylamino group, naphthylamino group, anthrylamino group and phenanthrylamino group. Of these, phenylamino group can be mentioned as a preferable group.

In the present invention, the term "heteroarylamino group" means a group formed by bonding of an amino group to the above-mentioned heteroaryl group. The heteroarylamino group includes, for example, furylamino group, thienylamino group, imidazolylamino group, oxazolylamino group, thiazolylamino group, pyridylamino group, indolylamino group, pyrimidinylamino group and pyridazinylamino group. Of these, pyridylamino group and furylamino group can be mentioned as preferable groups.

In the present invention, the term "arylaminocarbonyl group" means a group formed by bonding of an aminocarbonyl group to the above-mentioned aryl group. The arylaminocarbonyl group includes, for example, phenylaminocarbonyl group, biphenylaminocarbonyl group, naphthylaminocarbonyl group, anthrylaminocarbonyl group and phenanthrylaminocarbonyl group. Of these, phenylaminocarbonyl group can be mentioned as a preferable group.

In the present invention, as the formation of a cyclic group through a saturated or unsaturated carbon-carbon bond or a saturated or unsaturated carbon-carbon bond containing 1 to 3 heteroatoms selected from nitrogen atom, oxygen atom and sulfur atom, the formation of a 3- to 8-membered cyclic group, preferably the formation of a 4- to 7-membered cyclic group, can be mentioned. Here, the passage "the formation of a cyclic group through a saturated or unsaturated carbon-carbon bond" means the formation of, for example, a pyrrolidinyl group, a piperidinyl group, a pyrrolinyl group or a pyrrolyl group. The passage "the formation of a cyclic group through a saturated or unsaturated carbon-carbon bond containing 1 to 3 heteroatoms selected from nitrogen atom, oxygen atom and sulfur atom" means the formation of, for example, a piperazinyl group, a morpholinyl group, an imidazolinyl group or an imidazolyl group.

In the present invention, in the alkylene chain represented by $-(CH_2)_n-$, n is 0 to 3, namely, the lactam ring is a 4- to 7-membered ring. Preferably, n is 1 or 2, namely, the alkylene chain is a methylene group or an ethylene group.

Since the compound represented by general formula (1) has an asymmetric carbon atom and has an asymmetric phosphorus atom depending on the kind of the compound, the compound exists as a single optically active substance, a racemic modification or a mixture of optical isomers. Such a compound is obtained as the optically active substance, the racemic modification or the mixture of optical isomers. It should be understood that the compound of the present invention includes all of the optically active substance, the racemic modification and the mixture of optical isomers.

The pharmacologically acceptable salt of the compound of the present invention includes salts with mineral acids such as hydrochloric acid, sulfuric acid, etc.; salts with organic acids such as acetic acid, benzoic acid, succinic acid, fumaric acid, maleic acid, citric acid, acylcitric acids (e.g. benzoylcitric acid), lactic acid, acyllactic acid (e.g. benzoyllactic acid), tartaric acid, acyltartaric acids (e.g. benzoyltartaric acid), methanesulfonic acid, benzenesulfonic acid, etc.; salts with inorganic bases including inorganic metals such as sodium, potassium, lithium, calcium, etc.; and organic amines such as methylamine, ethylamine, diethanolamine, etc. These salts can be produced according to conventional processes.

It was revealed that the formation of a salt of the compound of general formula (1) with a dibasic acid such as tartaric acid, dibenzoyltartaric acid or the like contributes to the stability of the compound.

The compound represented by general formula (1) includes, for example, the following compounds:
(1) (3S)-3-amino-1-diaminophosphinyl-2-piperidone,
(2) (3S)-3-methylamino-1-diaminophosphinyl-2-piperidone,
(3) (3S)-3-(n-propyl)amino-1-diaminophosphinyl-2-piperidone,
(4) (3S)-3-isopropylamino-1-diaminophosphinyl-2-piperidone,
(5) (3S)-3-(n-butyl)amino-1-diaminophosphinyl-2-piperidone,
(6) (3S)-3-phenylamino-1-diaminophosphinyl-2-piperidone,
(7) (3S)-3-(2-pyridyl)amino-1-diaminophosphinyl-2-piperidone,
(8) (3S)-3-(3-butenyl)amino-1-diaminophosphinyl-2-piperidone,
(9) (3S)-3-cyclohexylamino-1-diaminophosphinyl-2-piperidone,
(10) (3S)-3-benzylamino-1-diaminophosphinyl-2-piperidone,
(11) (3S)-3-(4-methoxybenzyl)amino-1-diaminophosphinyl-2-piperidone,
(12) (3S)-3-(4-chlorobenzyl)amino-1-diaminophosphinyl-2-piperidone,
(13) (3S)-3-furfurylamino-1-diaminophosphinyl-2-piperidone,
(14) (3S)-3-(carboxymethyl)amino-1-diaminophosphinyl-2-piperidone,
(15) (3S)-3-(methoxycarbonylmethyl)amino-1-diaminophosphinyl-2-piperidone,
(16) (3S)-3-(carbamoylmethyl)amino-1-diaminophosphinyl-2-piperidone,
(17) (3S)-3-(methylaminocarbonylmethyl)amino-1-diaminophosphinyl-2-piperidone,
(18) (3S)-3-(2-methoxyethyl)amino-1-diaminophosphinyl-2-piperidone,
(19) (3S)-3-(2-hydroxyethyl)amino-1-diaminophosphinyl-2-piperidone,
(20) (3S)-3-(2-chloroethyl)amino-1-diaminophosphinyl-2-piperidone,
(21) (3S)-3-(2-aminoethyl)amino-1-diaminophosphinyl-2-piperidone,
(22) (3S)-3-(2-(methyamino)ethyl)amino-1-diaminophosphinyl-2-piperidone,
(23) (3S)-3-(2-(dimethyamino)ethyl)amino-1-diaminophosphinyl-2-piperidone,
(24) (3S)-3-(2-(phenylamino)ethyl)amino-1-diaminophosphinyl-2-piperidone,
(25) (3S)-3-(2-(2-pyridylamino)ethyl)amino-1-diaminophosphinyl-2-piperidone,
(26) (3S)-3-(2-(acetylamino)ethyl)amino-1-diaminophosphinyl-2-piperidone,
(27) (3S)-3-amino-1-bis(methylamino)phosphinyl-2-piperidone,
(28) (3S)-3-amino-1-bis(ethylamino)phosphinyl-2-piperidone,
(29) (3S)-3-amino-1-bis(n-propylamino)phosphinyl-2-piperidone,
(30) (3S)-3-amino-1-bis(n-hexylamino)phosphinyl-2-piperidone,
(31) (3S)-3-amino-1-amino(n-propylamino)phosphinyl-2-piperidone,
(32) (3S)-3-amino-1-bis(benzylamino)phosphinyl-2-piperidone,
(33) (3S)-3-amino-1-amino(benzylamino)phosphinyl-2-piperidone,
(34) (3S)-3-amino-1-bis((3-pyridylmethyl)amino)phosphinyl-2-piperidone,
(35) (3S)-3-amino-1-amino((3-pyridylmethyl)amino)phosphinyl-2-piperidone,
(36) (3S)-3-amino-1-amino((carboxymethyl)amino)phosphinyl-2-piperidone,
(37) (3S)-3-amino-1-amino((n-propylaminocarbonylmethyl)amino)phosphinyl-2-piperidone,
(38) (3S)-3-amino-1-amino((1-carboxyethyl)amino)phosphinyl-2-piperidone,
(39) (3S)-3-amino-1-amino((1-(n-propylaminocarbonyl)ethyl)amino)phosphinyl-2-piperidone,
(40) (3S)-3-amino-1-amino((1-(n-propylaminocarbonyl)isobutyl)amino)phosphinyl-2-piperidone,
(41) (3S)-3-amino-1-amino((2-methyl-1-(n-propylaminocarbonyl)butyl)amino)phosphinyl-2-piperidone,
(42) (3S)-3-amino-1-amino((3-methyl-1-(n-propylaminocarbonyl)butyl)amino)phosphinyl-2-piperidone,
(43) (3S)-3-amino-1-amino((2-hydroxy-1-(n-propylaminocarbonyl)ethyl)amino)phosphinyl-2-piperidone,
(44) (3S)-3-amino-1-amino((2-hydroxy-1-(n-propylaminocarbonyl)propyl)amino)phosphinyl-2-piperidone,
(45) (3S)-3-amino-1-amino((3-methylthio-1-(n-propylaminocarbonyl)propyl)amino)phosphinyl-2-piperidone,
(46) (3S)-3-amino-1-amino((2-mercapto-1-(n-propylaminocarbonyl)ethyl)amino)phosphinyl-2-piperidone,
(47) (3S)-3-amino-1-amino((2-carbamoyl-1-(n-propylaminocarbonyl)ethyl)amino)phosphinyl-2-piperidone,
(48) (3S)-3-amino-1-amino((2-carboxy-1-(n-propylaminocarbonyl)ethyl)amino)phosphinyl-2-piperidone,
(49) (3S)-3-amino-1-amino((3-carbamoyl-1-(n-propylaminocarbonyl)propyl)amino)phosphinyl-2-piperidone,
(50) (3S)-3-amino-1-amino((3-carboxy-1-(n-propylaminocarbonyl)propyl)amino)phosphinyl-2-piperidone,
(51) (3S)-3-amino-1-amino((2-phenyl-1-(n-propylaminocarbonyl)ethyl)amino)phosphinyl-2-piperidone,
(52) (3S)-3-amino-1-amino((2-(4-hydroxyphenyl)-1-(n-propylaminocarbonyl)ethyl)amino)phosphinyl-2-piperidone,
(53) (3S)-3-amino-1-amino((2-(3-indolyl)-1-(n-propylaminocarbonyl)ethyl)amino)phosphinyl-2-piperidone,
(54) (3S)-3-amino-1-amino((5-amino-1-(n-propylaminocarbonyl)pentyl)amino)phosphinyl-2-piperidone,
(55) (3S)-3-amino-1-amino((4-guanidino-1-(n-propylaminocarbonyl)butyl)amino)phosphinyl-2-piperidone,
(56) (3S)-3-amino-1-amino((2-(5-imidazolyl)-1-(n-propylaminocarbonyl)ethyl)amino)phosphinyl-2-piperidone,
(57) (3S)-3-amino-1-bis(phenylamino)phosphinyl-2-piperidone,
(58) (3S)-3-amino-1-amino(phenylamino)phosphinyl-2-piperidone,
(59) (3S)-3-amino-1-amino((4-methylphenyl)amino)phosphinyl-2-piperidone,
(60) (3S)-3-amino-1-amino((4-methoxyphenyl)amino)phosphinyl-2-piperidone,
(61) (3S)-3-amino-1-bis((4-methoxyphenyl)amino)phosphinyl-2-piperidone,
(62) (3S)-3-amino-1-amino((4-hydroxyphenyl)amino)phosphinyl-2-piperidone,
(63) (3S)-3-amino-1-amino((4-aminophenyl)amino)phosphinyl-2-piperidone,
(64) (3S)-3-amino-1-amino((2-methylaminophenyl)amino)phosphinyl-2-piperidone,

(65) (3S)-3-amino-1-amino(4-dimethylaminophenyl) amino)phosphinyl-2-piperidone,
(66) (3S)-3-amino-1-amino((4-carboxyphenyl)amino)phosphinyl-2-piperidone,
(67) (3S)-3-amino-1-amino((2-carboxyphenyl)amino)phosphinyl-2-piperidone,
(68) (3S)-3-amino-1-amino((4-methoxycarbonylphenyl)amino)phosphinyl-2-piperidone,
(69) (3S)-3-amino-1-amino((4-(n-propylaminocarbonyl)phenyl)amino)phosphinyl-2-piperidone,
(70) (3S)-3-amino-1-amino((4-chlorophenyl)amino)phosphinyl-2-piperidone,
(71) (3S)-3-amino-1-amino((4-cyanophenyl)amino)phosphinyl-2-piperidone,
(72) (3S)-3-amino-1-amino((4-nitrophenyl)amino)phosphinyl-2-piperidone,
(73) (3S)-3-amino-1-(3-butenylamino)amino-phosphinyl-2-piperidone,
(74) (3S)-3-amino-1-amino(cyclohexylamino)phosphinyl-2-piperidone,
(75) (3S)-3-amino-1-bis(acetylamino)phosphinyl-2-piperidone,
(76) (3S)-3-amino-1-amino(acetylamino)phosphinyl-2-piperidone,
(77) (3S)-3-amino-1-amino(cyclohexanecarbonylamino) phosphinyl-2-piperidone,
(78) (3S)-3-amino-1-bis(benzoylamino)phosphinyl-2-piperidone,
(79) (3S)-3-amino-1-amino(benzoylamino)phosphinyl-2-piperidone,
(80) (3S)-3-amino-1-amino((4-methylbenzoyl)amino)phosphinyl-2-piperidone,
(81) (3S)-3-amino-1-amino((4-methoxybenzoyl)amino) phosphinyl-2-piperidone,
(82) (3S)-3-amino-1-amino((4-chlorobenzoyl)amino)phosphinyl-2-piperidone,
(83) (3S)-3-amino-1-amino(butanoylamino)phosphinyl-2-piperidone,
(84) (3S)-3-amino-1-amino(phenoxyacetylamino)phosphinyl-2-piperidone,
(85) (3S)-3-amino-1-amino(cinnamoylamino)phosphinyl-2-piperidone,
(86) (3S)-3-amino-1-amino((3-phenylpropanoyl)amino) phosphinyl-2-piperidone,
(87) (3S)-3-amino-1-amino((phenylacetyl)amino)phosphinyl-2-piperidone,
(88) (3S)-3-amino-1-amino((4-fluorobenzoyl)amino)phosphinyl-2-piperidone,
(89) (3S)-3-amino-1-amino((4-nitrobenzoyl)amino)phosphinyl-2-piperidone,
(90) (3S)-3-amino-1-amino((t-butylacetyl)amino)phosphinyl-2-piperidone,
(91) (3S)-3-amino-1-amino(2-thenoylamino)phosphinyl-2-piperidone,
(92) (3S)-3-amino-1-amino(N'-ethylureido)phosphinyl-2-piperidone,
(93) (3S)-3-amino-1-amino(N'-phenylureido)phosphinyl-2-piperidone,
(94) (3S)-3-amino-1-amino(N'-4-bromophenylureido)phosphinyl-2-piperidone,
(96) (3S)-3-amino-1-amino(1-pyrrolidino)phosphinyl-2-piperidone,
(97) (3S)-3-amino-1-amino(3-thiazolidino)phosphinyl-2-piperidone,
(98) (3S)-3-amino-1-amino(1-(2-carboxypyrrolidino))phosphinyl-2-piperidone,
(99) (3S)-3-amino-1-amino(1-(2-(n-propylamino-carbonyl)pyrrolidino))phosphinyl-2-piperidone,
(100) (3S)-3-amino-1-amino(3-(4-carboxythiazolidino)) phosphinyl-2-piperidone,
(101) (3S)-3-amino-1-amino(3-(4-n-propylaminocarbonyl) thiazolidino)phosphinyl-2-piperidone,
(102) (3S)-3-n-propylamino-1-amino((carboxymethyl)amino)phosphinyl-2-piperidone,
(103) (3S)-3-n-propylamino-1-amino((n-propylaminocarbonylmethyl)amino)phosphinyl-2-piperidone,
(104) (3S)-3-n-propylamino-1-amino(acetylamino)phosphinyl-2-piperidone,
(105) (3S)-3-n-propylamino-1-amino(benzoylamino)phosphinyl-2-piperidone,
(106) (3S)-3-n-propylamino-1-amino(N'-ethylureido)phosphinyl-2-piperidone,
(107) (3S)-3-n-propylamino-1-amino(N'-phenylureido) phosphinyl-2-piperidone,
(108) (3S)-3-amino-1-diaminophosphinyl-2-perhydroazepinone,
(109) (3S)-3-amino-1-diaminophosphinyl-2-pyrrolidinone,
(110) (3R)-3-amino-1-diaminophosphinyl-2-piperidone,
(111) (2R)-3-amino-1-diaminophosphinyl-2-perhydroazepinone and
(112) (3R)-3-amino-1-diaminophosphinyl-2-pyrrolidinone.

The compound of the present invention can be produced as follows.

At first, an aldehyde or ketone corresponding to A is reacted with a compound of general formula (2):

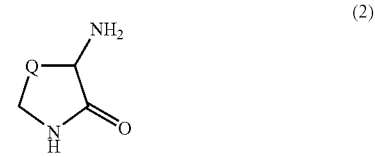

(2)

wherein Q is as defined above, which can easily be produced from an ester (e.g. an amino acid methyl ester having an amino group in its side chain) by cyclization (conversion to a lactam) using a base or the like or can be purchased as a reagent (e.g. α-amino-ε-caprolactam in which Q is —(CH$_2$)$_3$— and which is commercially available from Sigma Chemical Co.). The compound of general formula (2) is subjected to reduction after treatment with the aldehyde or ketone corresponding to A or to conventional substitution such as N-alkylation or N-arylation. The amine, which has the substituent introduced thereinto, is protected by a conventional method, in order to convert to a compound represented by general formula (3):

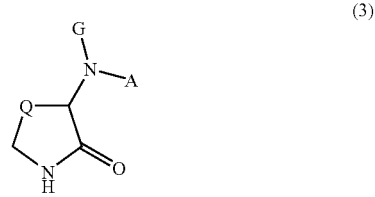

(3)

wherein Q and A are as defined above, and G is a conventional amino-protecting group. The amino-protecting group includes, for example, carbamate type protecting groups such as benzyloxycarbonyl groups whose benzyl group may be substituted by a lower alkyl group, a lower alkoxy group, an acyloxy group, a nitro group or a halogen atom, tert-butoxycarbonyl group, etc.; and amide type protecting groups such as formyl group, acetyl group, trifluoroacetyl group, etc. The carbamate type protecting groups are preferable, and benzyloxycarbonyl group is more preferable.

When A in general formula (3) is a lower alkyl group, a lower alkenyl group or a cycloalkyl group, the desired compound can be produced by reacting the aldehyde or ketone with the compound of general formula (2), followed by reduction. When A has a substituent unresistant to reduction or A is an aryl group or a heteroaryl group, the desired compound can be produced by N-alkylation or N-arylation by using, for example, an alkyl halide or an aryl halide, respectively, as a reagent.

An introduction of a substituent containing a diaminophosphinyl group into the compound of general formula (3) can be carried out by the following method to produce a compound represented by general formula (4):

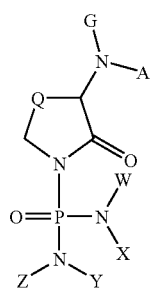

(4)

wherein Q, G, A, W, X, Y and Z are as defined above.

When the compound represented by general formula (4) has an unsubstituted diaminophosphinyl group, the compound represented by general formula (3) can be converted to the compound of general formula (4) by activation with n-butyllithium or the like followed by addition of phosphorus oxychloride and then ammonia, as in a well-known diaminophosphinylation (JP-A-2000-327689).

When the compound of general formula (4) is a derivative having a substituted diaminophosphinyl group formed by introduction of a lower alkyl group, an aryl group, a heteroaryl group, a lower alkenyl group or a cycloalkyl group into the amino group of a diaminophosphinyl group, or a derivative having a cyclic group (s) containing a nitrogen atom (s) and formed in a substituted diaminophosphinyl group, the compound of general formula (3) can be converted to the compound of general formula (4) by carrying out the same diaminophosphinylation as above except for adding a corresponding lower alkylamine, arylamine, heteroarylamine, lower alkenylamine or cycloalkylamine in place of ammonia.

When the compound of general formula (4) is a derivative having a substituted diaminophosphinyl group formed by introduction of a lower acyl group, an arylacyl group, a heteroarylacyl group, a lower alkylaminocarbonyl group or an arylaminocarbonyl group into the amino group of a diaminophosphinyl group, the compound of general formula (3) can be converted to the compound of general formula (4) by carrying out diaminophosphinylation followed by conventional acylation or conversion to a ureido. As an acylating agent, chloride, anhydride or the like of a corresponding carboxylic acid can be used. In the conversion to a ureide, a corresponding isocyanate can be used as a reagent. If necessary, these reactions may be carried out by using a base such as triethylamine, pyridine or the like as an additional reagent or a solvent.

The compound of general formula (4) obtained can be converted to the compound of the present invention represented by general formula (1):

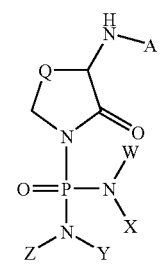

(1)

wherein Q, A, W, X, Y and Z are as defined above, by carrying out deprotection according to a conventional method as follows. For example, when the protecting group for the amine is a benzyloxycarbonyl group, it is removed by catalytic reduction. When the protecting group for the amine is a t-butoxycarbonyl group, it is removed by acid treatment.

For the isolation and purification of the desired compound from the reaction mixture obtained in each of the above production processes, conventional solvent extraction, concentration, crystallization, distillation, purification by suspension, various chromatographies and the like may be employed according to need.

The term "prophylactic or therapeutic agent for myelosuppression" used herein means an agent for treating leukopenia, erythropernia and thrombopenia by administering the agent to a human being or an animal to induce the production of hemocytes such as leukocytes, erythrocytes and thrombocytes in the body. Such an agent is for preventing or treating myelosuppression caused by radiotherapy, bone marrow transplantation, cancer chemical therapy, an antibiotic or the like, and anemias such as renal anemia, hemorrhagic anemia, hemolytic anemia, iron-deficiency anemia, etc. The agent can be used also for preventing or treating aplastic anemia, thrombopenia, infectious or viral diseases, leukopenia caused by malnutrition or the like, sudden thrombopenic purpura, etc. In the present invention, the agent is preferably used for preventing or treating leukopenia.

The term "agent for increasing the number of leukocytes" used herein means an agent having a property of increasing the production of leukocytes in the body. This agent can be used as a prophylactic or therapeutic agent for various diseases due to a decrease of the production of leukocytes caused by, for example, a congenital disease, irradiation with radiation, an aplastic disease, cancer chemical therapy or an antibiotic, and various diseases associated with the enhancement of leukocyte-disrupting function caused by an infectious disease, immune disorder or the like. Specifically, the agent can be used as a prophylactic and therapeutic agent for the decrease of the number of leukocytes in blood and as an agent for treating infectious diseases by increasing the number of leukocytes in blood to a number larger than the normal number. Here, the term "agent for treating infectious diseases" means an agent capable of increasing the production of leukocytes in the body to enhance protective effect on infection with bacteria, fungi and the like or exhibit therapeutic effect on the infection. The leukocytes include, for example, neutrophil, eosinophil, basophil, monocyte and lymphocyte.

When the compound of the present invention is used as a prophylactic or therapeutic agent for myelosuppression, a therapeutic agent for infectious diseases, an agent for increasing the number of leukocytes, or a dipeptidyl peptidase IV inhibitor, it is formulated singly or in admixture with an excipient or a carrier into a pharmaceutical preparation such as a suspension, an emulsion, an injection, an inhalation, tablets, pills, granules, fine granules, a powder, capsules, an oral solution, a suppository, an ophthalmic solution, an ophthalmic ointment, a percutaneous patch, an ointment, a trans-mucosal solution, a trans-mucosal patch, a spray or the like, and then orally or parenterally administered. As an additive such as the excipient or the carrier, a pharmaceutically acceptable additive is selected. The kind and composition of the additive are determined depending on an administration route and an administration method. For example, when the pharmaceutical preparation is an injection, sodium chloride and sugars (e.g. glucose and mannitol) can be usually used. When the pharmaceutical preparation is an oral preparation, starch, lactose, crystalline cellulose, magnesium stearate and the like can be used. If desired, assistants, stabilizers, wetting agents, emulsifiers, buffer solutions and other conventional additives may be contained in the above-mentioned pharmaceutical preparation.

Although the content of the compound in the pharmaceutical preparation is varied depending on the pharmaceutical preparation, it is usually 0.1 to 100% by weight, preferably 1 to 98% by weight. For example, when the pharmaceutical preparation is an injection, it is recommendable that the injection contains the active ingredient in a proportion of usually 0.1 to 30% by weight, preferably 1 to 10% by weight. When the pharmaceutical preparation is an oral preparation, the compound is used together with additives in the form of tablets, capsules, a powder, granules, a solution, a dry syrup or the like. The capsules, tablets, granules or powder contains the active ingredient in a proportion of usually 5 to 100% by weight, preferably 25 to 98% by weight.

Although the dose is determined depending on the age, sex, weight and symptom of a patient, a purpose of treatment, and the like, the therapeutic dose is usually 0.001 to 200 mg/kg/day in the case of parenteral administration, and is 0.01 to 500 mg/kg/day, preferably 0.1 to 100 mg/kg/day, in the case of oral administration. The compound is administered in such a dose in one portion or in 2 to 5 portions.

In the case of the pharmaceutical preparation, the prophylactic or therapeutic agent for myelosuppression or agent for increasing the number of leukocytes, i.e., the α-amino-N-(diaminophosphinyl)lactam derivative of the present invention can be used for preventive administration to a patient who is expected to suffer myelosuppression. It is known that for example, when various diseases are treated by employing radiotherapy, antitumor agents and antibiotics, the malfunction of bone marrow is very frequently caused. To a patient who is expected to suffer such malfunction of bone marrow, the α-amino-N-(diaminophosphinyl)lactam derivative of the present invention is administered preparatorily before the treatment or at the time of the treatment, whereby effects can be obtained.

Examples of the synthesis of the compounds of the present invention and examples of pharmacological experiment on the compounds are described below as working examples, but they are not intended in any way to limit the scope of the present invention.

In NMR, when there is no internal standard reference material, a peak due to a solvent (4.65 ppm in the case of $D_2O$, 2.49 ppm in the case of DMSO-$d_6$, and 3.30 ppm in the case of $CD_3OD$) was employed as a base peak. When the synthetic product was observed as a mixture of two forms owing to rotational hindrance, the two forms were named A-form and B-form and NMR data of A-form and those of B-form were separately described to the best of our ability. When the synthetic product was a mixture of stereoisomers, the isomers were named stereoisomer A and stereoisomer B and NMR data of stereoisomer A and those of stereoisomer B were separately described to the best of our ability.

EXAMPLE 1

Synthesis of (3S)-3-amino-1-diaminophosphinyl-2-piperidone

Palladium black (0.15 g) was added to a suspension of (3S)-3-benzyloxycarbonylamino-1-diaminophosphinyl-2-piperidone (2.50 g, 7.66 mmol) in ethanol (30 mL), and the resulting mixture was stirred under a hydrogen atmosphere at room temperature for 16 hours and then at an external temperature of 60° C. for 1 hour.

After the catalyst in the reaction mixture was filtered off, the solvent was concentrated under reduced pressure to obtain the desired compound (1.42 g, 97%).

$^1$H-NMR ($D_2O$, 4.65 ppm) 3.47 (1H, t, J=6.0 Hz), 3.46, (1H, t, J=6.0 Hz), 3.35 (1H, dd, J=10.2 Hz, 6.8 Hz), 2.01~2.09 (1H, m), 1.68~1.82 (2H, m), 1.39~1.49 (1H, m). MS (FAB+, Gly) m/z: 193[M+H]$^+$, 215[M+Na]$^+$.

EXAMPLE 2

Synthesis of (3S)-3-benzyloxycarbonylamino-1-bis(methylamino)phosphinyl-2-piperidone A solution of (3S)-3-benzyloxycarbonylamino-2-piperidone (3.73 g, 15.02 mmol) in tetrahydrofuran (60 mL) was cooled at an external temperature of −78° C., followed by adding dropwise thereto an n-butyllithium-hexane solution (1.54 M, 9.3 mL, 14.32 mmol) over a period of 20 minutes, and the resulting mixture was stirred at the same temperature for 20 minutes. Subsequently, a solution of phosphorus oxychloride (2.30 g, 15.00 mmol) in tetrahydrofuran (10 mL) was added thereto and stirred for 20 minutes, after which a solution of methylamine (a 40% aqueous solution, 5.8 mL, 74.69 mmol) in tetrahydrofuran (50 mL) was added thereto after being dried over potassium carbonate, and the resulting mixture was stirred for 10 minutes.

The reaction mixture was concentrated under reduced pressure and water was added thereto, followed by extraction with chloroform. The chloroform solution was washed with a saturated aqueous sodium chloride solution and dried over anhydrous sodium sulfate, and then the solvent was concentrated under reduced pressure to obtain a light-yellow oil. The oil was purified by a Diaion HP-20 (200 mL; elution with a water-methanol gradient) column chromatography to obtain the desired compound (1.98 g, 37%).

$^1$H-NMR ($CDCl_3$, internal standard TMS) 7.30~7.37 (5H, m), 5.61 (1H, brd, J=5.4 Hz), 5.12 (2H, s), 4.26~4.31 (1H, m), 3.93 (1H, qd, J=5.3 Hz, 13.2 Hz), 3.48~3.56 (1H, m), 3.06~3.15 (1H, m), 2.98~3.06 (1H, m), 2.61 (3H, t, J=5.9

Hz), 2.58 (3H, t, J=5.9 Hz), 2.47~2.55 (1H, m), 1.86~1.95 (2H, m), 1.55 (1H, tt, J=13.2 Hz, 8.3 Hz). MS (FAB+, NBA) m/z: 355[M+H]$^+$.

EXAMPLE 3

Synthesis of (3S)-3-amino-1-bis(methylamino)phosphinyl-2-piperidone

Palladium black (52 mg) was added to a solution of (3S)-3-benzyloxycarbonylamino-1-bis(methylamino)phosphinyl-2-piperidone (524.1 mg, 1.4791 mmol) in methanol (5.2 mL), and the resulting mixture was stirred at room temperature for 3 hours under a hydrogen atmosphere.

After the catalyst in the reaction mixture was filtered off, the solvent was concentrated under reduced pressure to obtain the desired compound (315.1 mg, 97%).

$^1$H-NMR (CDCl$_3$, internal standard TMS) 3.75 (1H, dddd, J=13.2 Hz, 7.3 Hz, 5.4 Hz, 4.4 Hz), 3.61~3.63 (1H, m), 3.45 (1H, dd, J=11.7 Hz, 7.3 Hz), 3.05~3.15 (2H, m), 2.63 (3H, dd, J=13.2 Hz, 5.4 Hz), 2.60 (3H, dd, J=13.2 Hz, 5.4 Hz), 2.24~2.31 (1H, m), 1.83~1.97 (2H, m), 1.76 (2H, brs), 1.55 (1H, dddd, J=13.2 Hz, 11.7 Hz, 8.8 Hz, 7.3 Hz). MS (FAB+, NBA) m/z: 221 [M+H]$^+$, 190 [M-MeNH2+H]$^+$.

EXAMPLE 4

Synthesis of (3S)-3-benzyloxycarbonylamino-1-bis (ethylamino)phosphinyl-2-piperidone A solution of (3S)-3-benzyloxycarbonylamino-2-piperidone (3.73 g, 15.02 mmol) in tetrahydrofuran (60 mL) was cooled at an external temperature of −78° C., followed by adding dropwise thereto an n-butyllithium-hexane solution (1.54 M, 9.3 mL, 14.32 mmol) over a period of 15 minutes, and the resulting mixture was stirred at the same temperature for 20 minutes. Subsequently, a solution of phosphorus oxychloride (2.30 g, 15.00 mmol) in tetrahydrofuran (6 mL) was added thereto and stirred for 30 minutes, after which a solution of ethylamine (a 70% aqueous solution, 5.47 mL, 84.92 mmol) in tetrahydrofuran (50 mL) was added thereto after being dried over potassium carbonate, and the resulting mixture was stirred for 5 minutes.

The reaction mixture was concentrated under reduced pressure and water was added thereto, followed by extraction with chloroform. The chloroform solution was washed with a saturated aqueous sodium chloride solution and dried over anhydrous sodium sulfate, and then the solvent was concentrated under reduced pressure to obtain a light-yellow oil. The oil was purified by a silica gel (150 g, chloroform: methanol=19:1) column chromatography to obtain an oil. This oil was purified in 6 portions by a Sephadex LH-20 (180 mL, methanol) column chromatography, and then purified again by a silica gel (100 g, chloroform:methanol=29:1~19:1~14:1) column chromatography to obtain an oil (1.95 g). The oil obtained was crystallized from ethanol-ether to obtain the desired compound (1.78 g, 31%).

$^1$H-NMR (CDCl$_3$, internal standard TMS) 7.29~7.33 (5H, m), 5.60 (1H, brd, J=4.9 Hz), 5.13 (2H, s), 4.22~4.28 (1H, m), 3.95 (1H, qd, J=5.9 Hz, 13.2 Hz), 3.47~3.56 (1H, m), 3.12~3.18 (1H, m), 2.89~3.08 (5H, m), 2.48~2.54 (1H, m), 1.84~1.96 (2H, m), 1.53 (1H, tt, J=13.2 Hz, 8.3 Hz), 1.12 (3H, t, J=6.8 Hz), 1.11 (3H, t, J=6.8 Hz). MS (FAB+, NBA) m/z: 383 [M+H]$^+$.

EXAMPLE 5

Synthesis of (3S)-3-amino-1-bis(ethylamino)phosphinyl-2-piperidone

Palladium black (60 mg) was added to a solution of (3S)-3-benzyloxycarbonylamino-1-bis(ethylamino)phosphinyl-2-piperidone (600.3 mg, 1.5698 mmol) in methanol (6 mL), and the resulting mixture was stirred at room temperature for 3 hours under a hydrogen atmosphere.

After the catalyst in the reaction mixture was filtered off, the solvent was concentrated under reduced pressure to obtain the desired compound (382.3 mg, 98%).

$^1$H-NMR (CDCl$_3$, internal standard TMS) 3.75 (1H, dddd, J=13.2 Hz, 7.4 Hz, 5.4 Hz, 3.9 Hz), 3.61~3.69 (1H, m), 3.42 (1H, dd, J=11.2 Hz, 6.8 Hz), 3.05~3.18 (2H, m), 2.91~3.06 (4H, m), 2.23~2.30 (1H, m), 1.80~1.96 (2H, m), 1.73 (2H, brs), 1.53 (1H, dddd, J=13.2 Hz, 11.2 Hz, 8.8 Hz, 6.8 Hz), 1.13 (3H, t, J=7.8 Hz), 1.12 (3H, t, J=7.8 Hz). MS (FAB+, NBA) m/z: 249 [M+H]$^+$, 204 [M-EtNH$_2$+H]$^+$.

EXAMPLE 6

Synthesis of (3S)-3-benzyloxycarbonylamino-1-bis (n-propylamino)phosphinyl-2-piperidone A solution of (3S)-3-benzyloxycarbonylamino-2-piperidone (3.73 g, 15.02 mmol) in tetrahydrofuran (45 mL) was cooled at an external temperature of −78° C., followed by adding dropwise thereto an n-butyllithium-hexane solution (1.54 M, 9.3 mL, 14.32 mmol) over a period of 15 minutes, and the resulting mixture was stirred at the same temperature for 20 minutes. Subsequently, a solution of phosphorus oxychloride (2.30 g, 15.00 mmol) in tetrahydrofuran (5 mL) was added thereto and stirred for 30 minutes, after which n-propylamine (d=0.719, 5.2 mL, 63.25 mmol) was added thereto and stirred for 1 hour.

The reaction mixture was concentrated under reduced pressure and water was added thereto, followed by extraction with chloroform. The chloroform solution was washed with a saturated aqueous sodium chloride solution and dried over anhydrous sodium sulfate, and then the solvent was concentrated under reduced pressure to obtain a light-yellow oil. The oil was purified twice by a silica gel (100 g, chloroform: methanol=29:1~19:1) column chromatography to obtain the desired compound (0.98 g, 16%).

$^1$H-NMR (CDCl$_3$, internal standard TMS) 7.30~7.37 (5H, m), 5.58~5.63 (1H, m), 5.12 (2H, s), 4.22~4.29 (1H, m), 3.96 (1H, qd, J=5.9 Hz, 13.7 Hz), 3.46~3.55 (1H, m), 3.17~3.24 (1H, m), 3.03~3.11 (1H, m), 2.83~2.95 (4H, m), 2.49~2.57 (1H, m), 1.84~1.96 (2H, m), 1.43~1.57 (5H, m), 0.89 (3H, t, J=7.3 Hz), 0.88 (3H, t, J=7.3 Hz). MS (FAB+, Gly) m/z: 411 [M+H]$^+$.

EXAMPLE 7

Synthesis of (3S)-3-amino-1-bis(n-propylamino) phosphinyl-2-piperidone

Palladium black (50 mg) was added to a solution of (3S)-3-benzyloxycarbonylamino-1-bis(n-propylamino) phosphinyl-2-piperidone (500.0 mg, 1.2182 mmol) in methanol (5 mL), and the resulting mixture was stirred at room temperature for 3 hours under a hydrogen atmosphere.

After the catalyst in the reaction mixture was filtered off, the solvent was concentrated under reduced pressure to obtain the desired compound (328.3 mg, 98%).

¹H-NMR (CDCl₃, internal standard TMS) 3.70~3.78 (1H, m), 3.61~3.69 (1H, m), 3.43 (1H, dd, J=11.2 Hz, 6.8 Hz), 3.13~3.27 (2H, m), 2.81~2.99 (4H, m), 2.23~2.31 (1H, m), 2.16 (2H, brs), 1.80~1.96 (2H, m), 1.43~1.60 (5H, m), 0.90 (3H, t, J=7.3 Hz), 0.89 (3H, t, J=7.3 Hz). MS (FAB+, NBA) m/z: 277 [M+H]⁺, 218 [M-PrNH₂+H]⁺.

EXAMPLE 8

Synthesis of (3S)-3-benzyloxycarbonylamino-1-bis(n-hexylamino)phosphinyl-2-piperidone A solution of (3S)-3-benzyloxycarbonylamino-2-piperidone (2.48 g, 9.99 mmol) in tetrahydrofuran (25 mL) was cooled at an external temperature of −78° C., followed by adding dropwise thereto an n-butyllithium-hexane solution (1.54 M, 6.2 mL, 9.548 mmol) over a period of 10 minutes, and the resulting mixture was stirred at the same temperature for 1.5 hours. Subsequently, a solution of phosphorus oxychloride (1.53 g, 9.98 mmol) in tetrahydrofuran (5 mL) was added thereto and stirred for 1.25 hours, after which n-hexylamine (d=0.76, 6.0 mL, 45.06 mmol) was added thereto and the resulting mixture was stirred at room temperature for 10 minutes.

The reaction mixture was concentrated under reduced pressure and water was added thereto, followed by extraction with ethyl acetate. The ethyl acetate solution was washed with a saturated aqueous sodium chloride solution and dried over anhydrous sodium sulfate, and then the solvent was concentrated under reduced pressure to obtain a light-yellow oil. The oil was purified by a silica gel (150 g, chloroform:ethyl acetate=9:1~4:1) column chromatography to obtain the desired compound (2.08 g, 42%).

¹H-NMR (CDCl₃, internal standard TMS) 7.29~7.40 (5H, m), 5.60 (1H, brd, J=4.9 Hz), 5.12 (2H, s), 4.21~4.29 (1H, m), 3.95 (1H, qd, J=5.8 Hz 13.2 Hz), 3.46~3.54 (1H, m), 3.16 (1H, q, J=7.3 Hz), 3.03 (1H, q, J=7.3 Hz), 2.82~2.98 (4H, m), 2.48~2.58 (1H, m), 1.85~1.94 (2H, m), 1.41~1.56 (5H, m), 1.20~1.32 (12H, m), 0.87 (6H, t, J=6.8 Hz). MS (FAB+, NBA) m/z: 495 [M+H]⁺.

EXAMPLE 9

Synthesis of (3S)-3-amino-1-bis(n-hexylamino)phosphinyl-2-piperidone

Palladium black (31 mg) was added to a solution of (3S)-3-benzyloxycarbonylamino-1-bis(n-hexylamino)phosphinyl-2-piperidone (310.9 mg, 0.6286 mmol) in methanol (3 mL), and the resulting mixture was stirred at room temperature for 1 hour under a hydrogen atmosphere.

After the catalyst in the reaction mixture was filtered off, the solvent was concentrated under reduced pressure to obtain the desired compound (226.0 mg, 100%).

¹H-NMR (CDCl₃, internal standard TMS) 3.74 (1H, dddd, J=13.2 Hz, 7.3 Hz, 5.4 Hz, 3.9 Hz), 3.60~3.68 (1H, m), 3.41 (1H, dd, J=11.2 Hz, 6.8 Hz), 3.17 (1H, brq, J=6.8 Hz), 3.10 (1H, brq, J=6.8 Hz), 2.82~3.02 (4H, m), 2.23~2.31 (1H, m), 1.80~1.96 (2H, m), 1.53 (1H, dddd, J=13.2 Hz, 11.2 Hz, 8.8 Hz, 6.8 Hz), 1.41~1.48 (4H, m), 1.20~1.34 (12H, m), 0.88 (6H, t, J=6.8 Hz). MS (FAB+, NBA) m/z: 361 [M+H]⁺, 260 [M-C₆H₁₃NH₂+H]⁺.

EXAMPLE 10

Synthesis of (3S)-3-benzyloxycarbonylamino-1-bis(phenylamino)phosphinyl-2-piperidone A solution of (3S)-3-benzyloxycarbonylamino-2-piperidone (2.48 g, 9.99 mmol) in tetrahydrofuran (30 mL) was cooled at an external temperature of −78° C., followed by adding dropwise thereto an n-butyllithium-hexane solution (1.50 M, 6.5 mL, 9.75 mmol) over a period of 20 minutes, and the resulting mixture was stirred at the same temperature for 30 minutes. Subsequently, a solution of phosphorus oxychloride (1.53 g, 9.98 mmol) in tetrahydrofuran (3 mL) was added thereto and stirred for 20 minutes, after which aniline (d=1.022, 4.1 mL, 44.99 mmol) was added thereto and stirred for 1.5 hours.

The reaction mixture was concentrated under reduced pressure and an aqueous sodium chloride solution was added thereto, followed by extraction with chloroform. The chloroform solution was washed with a saturated aqueous sodium chloride solution and dried over anhydrous sodium sulfate, and then the solvent was concentrated under reduced pressure to obtain a light-yellow oil. The oil was purified by a silica gel (150 g, chloroform:ethyl acetate=4:1~3:1~2:1) column chromatography and the resulting oil was crystallized from ether-n-hexane. The resulting crystals were washed with ethyl acetate-n-hexane to obtain the desired compound (1.21 g, 25%).

¹H-NMR (CDCl₃, internal standard TMS) 7.31~7.37 (5H, m), 7.19~7.24 (4H, m), 7.09~7.15 (4H, m), 6.99 (2H, t, J=7.3 Hz), 6.13 (1H, brd, J=7.3 Hz), 6.09 (1H, brd, J=7.3 Hz), 5.53 (1H, brd, J=5.4 Hz), 5.03~5.12 (2H, m), 4.12~4.22 (1H, m), 3.95~4.05 (1H, m), 3.45~3.55 (1H, m), 2.26~2.35 (1H, m), 1.60~1.82 (2H, m), 1.21~1.32 (1H, m). MS (FAB+, NBA) m/z: 479 [M+H]⁺.

EXAMPLE 11

Synthesis of (3S)-3-amino-1-bis(phenylamino)phosphinyl-2-piperidone

Palladium black (20 mg) was added to a solution of (3S)-3-benzyloxycarbonylamino-1-bis(phenylamino)phosphinyl-2-piperidone (200.2 mg, 0.4184 mmol) in methanol (4 mL), and the resulting mixture was stirred overnight at room temperature under a hydrogen atmosphere.

After the catalyst in the reaction mixture was filtered off, the solvent was concentrated under reduced pressure to obtain the desired compound (142.9 mg, 99%).

¹H-NMR (CDCl₃, internal standard TMS) 7.07~7.26 (8H, m), 6.92~7.02 (2H, m), 6.04 (1H, brs) 5.99 (1H, brs), 3.78~3.86 (1H, m), 3.63~3.70 (1H, m), 3.33 (1H, dd, J=11.2 Hz, 6.8 Hz), 2.11~2.19 (1H, m), 1.81 (2H, brs), 1.70~1.80 (2H, m), 1.33~1.44 (1H, m). MS (FAB+, NBA) m/z: 345 [M+H]⁺, 252 [M-PhNH₂+H]⁺.

EXAMPLE 12

Synthesis of (3S)-3-benzyloxycarbonylamino-1-bis(4-methoxyphenylamino)phosphinyl-2-piperidone A solution of (3S)-3-benzyloxycarbonylamino-2-piperidone (1.24 g, 4.99 mmol) in tetrahydrofuran (15 mL) was cooled at an external temperature of −78° C., followed by adding dropwise thereto an n-butyllithium-hexane solution (1.59 M, 3.0 mL, 4.77 mmol) over a period of 10 minutes, and the resulting mixture was stirred at the same temperature for 30 minutes. Subsequently, a solution of phosphorus oxychloride (0.77 g, 5.02 mmol) in tetrahydrofuran (3 mL) was added thereto and stirred for 30 minutes, after which 4-methoxyaniline (2.70 g, 21.92 mmol) was added thereto and the resulting mixture was stirred at room temperature for 2 hours.

An aqueous sodium chloride solution was added to the reaction mixture, followed by extraction with ethyl acetate. The ethyl acetate solution was washed with a saturated aqueous sodium chloride solution and dried over anhydrous sodium sulfate, and then the solvent was concentrated under reduced pressure to obtain a light-yellow oil. The oil was purified by a silica gel (50 g, chloroform:ethyl acetate=9:1~4:1~3:1~2:1) column chromatography to obtain the desired compound (0.39 g, 14%).

$^1$H-NMR (CDCl$_3$, internal standard TMS) 7.30~7.38 (5H, m), 7.05 (4H, d, J=8.8 Hz), 6.77 (4H, td, J=2.0 Hz, 8.8 Hz), 5.73~5.80 (2H, m), 5.56 (1H, brd, J=5.9 Hz), 5.07~5.16 (2H, m), 4.13~4.20 (1H, m), 3.91 (1H, tdd, J=6.4 Hz, 13.7 Hz, 4.9 Hz), 3.75 (3H, s), 3.74 (3H, s), 3.37~3.45 (1H, m), 2.24~2.32 (1H, m), 1.67~1.75 (1H, m), 1.49~1.60 (1H, m), 1.19~1.22 (1H, m). MS (FAB+, NBA) m/z: 539 [M+H]$^+$.

EXAMPLE 13

Synthesis of (3S)-3-amino-1-bis(4-methoxyphenylamino)phosphinyl-2-piperidone

Palladium black (30 mg) was added to a solution of (3S)-3-benzyloxycarbonylamino-1-bis(4-methoxyphenylamino)phosphinyl-2-piperidone (150.2 mg, 0.2789 mmol) in methanol (5 mL), and the resulting mixture was stirred overnight at room temperature under a hydrogen atmosphere.

After the catalyst in the reaction mixture was filtered off, the solvent was concentrated under reduced pressure to obtain the desired compound (108.8 mg, 96%).

$^1$H-NMR (DMSO-D$_6$, 2.49 ppm) 7.43 (1H, brd, J=8.8 Hz), 7.27 (1H, brd, J=8.8 Hz), 7.02 (2H, d, J=8.8 Hz), 6.99 (2H, d, J=8.8 Hz), 6.78 (2H, d, J=8.8 Hz), 6.78 (2H, d, J=8.8 Hz), 3.66 (6H, s), 3.43~3.51 (1H, m), 3.37 (1H, dd, J=13.7 Hz, 6.8 Hz), 3.32 (2H, brs), 3.23 (1H, dd, J=11.2 Hz, 6.8 Hz), 1.92~2.00 (1H, m), 1.55~1.70 (2H, m), 1.17~1.27 (1H, m). MS (FAB+, NBA) m/z: 405 [M+H]$^+$, 282 [M-MeOC$_6$H$_4$NH$_2$+H]$^+$.

EXAMPLE 14

Synthesis of (3S, P (RS))-3-benzyloxy-carbonylamino-1-amino(n-propylamino)phosphinyl-2-piperidone A solution of (3S)-3-benzyloxycarbonylamino-2-piperidone (3.73 g, 15.02 mmol) in tetrahydrofuran (60 mL) was cooled at an external temperature of −78° C., followed by adding dropwise thereto an n-butyllithium-hexane solution (1.54 M, 9.3 mL, 14.32 mmol) over a period of 15 minutes, and the resulting mixture was stirred at the same temperature for 30 minutes. Subsequently, a solution of phosphorus oxychloride (2.30 g, 15.00 mmol) in tetrahydrofuran (10 mL) was added thereto and stirred for 30 minutes, after which a solution of n-propylamine (d=0.719, 0.93 mL, 11.31 mmol) and triethylamine (d=0.7225, 1.58 mL, 11.28 mmol) in tetrahydrofuran (5 mL) was slowly added thereto and stirred for 10 minutes. Then, a solution of ammonia in chloroform (1M, 40 mL, 40.00 mmol) was added thereto and stirred for 10 minutes.

An aqueous sodium chloride solution and then n-hexane were added to the reaction mixture to form two separate layers. After the aqueous layer was extracted with chloroform, the combined organic layer was concentrated under reduced pressure and purified by a Diaion HP-20 (200 mL, elution with a water-methanol gradient) column chromatography to obtain the desired compound (0.34 g, 6%).

$^1$H-NMR (CDCl$_3$, internal standard TMS) 7.30~7.39 (5H, m), 5.63 (1H, brd, J=4.9 Hz), 5.12 (2H, s), 4.20~4.28 (1H, m), 3.90 (1H, qd, J=5.9 Hz, 13.7 Hz), 3.52~3.60 (1H, m), 3.30and3.25 (2H, brs), 3.14and3.08 (1H, brq, J=7.8 Hz), 2.78~2.96 (2H, m), 2.46~2.54 (1H, m), 1.87~1.95 (2H, m), 1.53~1.63 (1H, m), 1.43~1.52 (2H, m) 0.89and0.88 (3H, t, J=7.3 Hz). MS (FAB+, NBA) m/z: 369 [M+H]$^+$.

EXAMPLE 15

Synthesis of (3S, P (RS))-3-amino-1-amino(n-propylamino)phosphinyl-2-piperidone

Palladium black (16 mg) was added to a solution of (3S)-3-benzyloxycarbonylamino-1-amino(n-propylamino)phosphinyl-2-piperidone (161.1 g, 0.4373 mmol) in methanol (3 mL), and the resulting mixture was stirred at room temperature for 50 minutes under a hydrogen atmosphere.

After the catalyst in the reaction mixture was filtered off, the solvent was concentrated under reduced pressure to obtain the desired compound (98.6 mg, 96%).

$^1$H-NMR (DMSO-D$_6$, 2.49 ppm) 4.22~4.31 (1H, m), 4.19 (1H, brs), 3.49~3.60 (1H, m), 3.37~3.47 (1H, m), 3.26~3.36 (4H, m), 2.58~2.68 (2H, m), 1.98~2.06 (1H, m), 1.67~1.74 (2H, m), 1.36~1.44 (1H, m), 1.29~1.39 (2H, m) 0.81and0.79 (3H, t, J=7.3 Hz) MS (FAB+, NBA) m/z: 235 [M+H]$^+$, 176 [M-PrNH2+H]$^+$.

EXAMPLE 16

Synthesis of (3S, P (R or S))-benzyloxy-carbonylamino-1-amino(phenylamino)phosphinyl-2-piperidone and (3S, P (S or R))-benzyloxycarbonylamino-1-amino(phenylamino)phosphinyl-2-piperidone A solution of (3S)-3-benzyloxycarbonylamino-2-piperidone (2.48 g, 9.99 mmol) in tetrahydrofuran (30 mL) was cooled at an external temperature of −78° C., followed by adding dropwise thereto an n-butyllithium-hexane solution (1.59 M, 6.2 mL, 9.86 mmol) over a period of 20 minutes, and the resulting mixture was stirred at the same temperature for 30 minutes. Subsequently, a solution of phosphorus oxychloride (1.53 g, 9.98 mmol) in tetrahydrofuran (3 mL) was added thereto and stirred for 30 minutes, after which aniline (d=1.022, 1.8 mL, 19.75 mmol) was added thereto and stirred for 1 hour. Then, a solution of ammonia in chloroform (1.15 M, 17.4 mL, 20.01 mmol) was added thereto and stirred for 30 minutes.

The reaction mixture was concentrated under reduced pressure and an aqueous sodium chloride solution was added thereto, followed by extraction with chloroform. The chloroform solution was washed with a saturated aqueous sodium chloride solution and dried over anhydrous sodium sulfate, and then the solvent was concentrated under reduced pressure to obtain a light-yellow oil. The oil was purified twice by a silica gel (100 g, chloroform ethyl acetate=4:1~3:1~2:1) column chromatography to obtain the desired compounds, i.e., (3S, P (R or S))-benzyloxycarbonylamino-1-amino(phenylamino)phosphinyl-2-piperidone (0.10 g, 2%) and (3S, P (S or R))-benzyloxycarbonylamino-1-amino (phenylamino)phosphinyl-2-piperidone (0.06 g, 1%).

(3S, P (R or S))-benzyloxycarbonylamino-1-amino (phenylamino)phosphinyl-2-piperidone $^1$H-NMR (CDCl$_3$, internal standard TMS) 7.30~7.38 (5H, m), 7.23 (2H, t, J=7.8 Hz), 7.05 (2H, d, J=7.8 Hz), 7.01 (1H, t, J=7.8 Hz), 5.52 (1H, brd, J=6.8 Hz), 5.43 (1H, brd, J=2.0 Hz), 5.08~5.14 (2H, m), 4.16~4.22 (1H, m), 3.92 (1H, tdd, J=6.8 Hz, 13.7 Hz, 4.8 Hz), 3.54 (2H, brs), 3.46~3.53 (1H, m), 2.20~2.28 (1H, m), 1.70~1.78 (1H, m), 1.42~1.52 (1H, m), 1.22~1.31 (1H, m) MS (FAB+, NBA) m/z: 403 [M+H]$^+$. MS (FAB−, NBA) m/z: 401 [M−H]$^-$.

(3S, P (S or R))-benzyloxycarbonylamino-1-amino (phenylamino)phosphinyl-2-piperidone $^1$H-NMR (CDCl$_3$, internal standard TMS) 7.30~7.38 (5H, m), 7.23 (2H, t, J=7.8 Hz), 7.01 (2H, d, J=7.8 Hz), 7.00 (1H, t, J=7.8 Hz), 5.48~5.52 (1H, m), 5.44 (1H, brd, J=7.3 Hz), 5.10 (2H, s), 3.94~4.03 (1H, m), 3.88~3.94 (1H, m), 3.55 (2H, brs), 3.50~3.54 (1H, m), 2.40~2.47 (1H, m), 1.85~1.94 (1H, m), 1.73~1.83 (1H, m), 1.52~1.63 (1H, m). MS (FAB+, NBA) m/z: 403 [M+H]$^+$. MS (FAB−, NBA) m/z: 401 [M−H]$^-$.

EXAMPLE 17

Synthesis of (3S, P (R or S))-3-amino-1-amino(phenylamino)phosphinyl-2-piperidone Palladium black (10 mg) was added to a solution of (3S, P (R or S))-3-benzyloxycarbonylamino-1-amino(phenylamino)phosphinyl-2-piperidone (71.0 mg, 0.1764 mmol) in methanol (7 mL), and the resulting mixture was stirred overnight at room temperature under a hydrogen atmosphere.

After the catalyst in the reaction mixture was filtered off, the solvent was concentrated under reduced pressure to obtain the desired compound (47.0 mg, 99%).

$^1$H-NMR (CD$_3$OD, 3.30 ppm) 7.20 (2H, t, J=7.8 Hz), 7.05 (2H, dd, J=7.8 Hz, 1.0 Hz), 6.93 (1H, t, J=7.8 Hz), 3.75 (1H, qd, J=5.9 Hz, 12.8 Hz) 3.56~3.63 (1H, m), 3.51 (1H, dd, J=11.7 Hz, 6.8 Hz), 2.06~2.14 (1H, m), 1.64~1.84 (2H, m), 1.21~1.30 (1H, m). MS (FAB+, NBA) m/z: 269 [M+H]$^+$.

EXAMPLE 18

Synthesis of (3S, P (S or R))-amino-1-amino(phenylamino)phosphinyl-2-piperidone

Palladium black (5 mg) was added to a solution of (3S, P (S or R))-3-benzyloxycarbonylamino-1-amino(phenylamino)phosphinyl-2-piperidone (25.3 mg, 0.0627 mmol) in methanol (2 mL), and the resulting mixture was stirred overnight at room temperature under a hydrogen atmosphere.

After the catalyst in the reaction mixture was filtered off, the solvent was concentrated under reduced pressure to obtain the desired compound (16.9 mg, 100%).

$^1$H-NMR (CDCl$_3$, internal standard TMS) 7.23 (2H, t, J=7.8 Hz), 7.02 (2H, d, J=7.8), 6.99 (1H, t, J=7.8 Hz), 5.44 (1H, brd, J=7.3 Hz), 3.64~3.79 (2H, m), 3.56 (2H, brs), 3.16 (1H, dd, J=11.2 Hz, 6.8 Hz), 2.12~2.20 (1H, m), 1.84~1.93 (1H, m), 1.48~1.75 (4H, m). MS (FAB+, NBA) m/z: 269 [M+H]$^+$.

EXAMPLE 19

Synthesis of (3S)-3-amino-2-piperidone

To a solution of (3S)-3-benzyloxycarbonylamino-2-piperidone (15.00 g, 60.42 mmol) in methanol (100 mL) was added 10% palladium-activated carbon (2.00 g), and the resulting mixture was stirred at room temperature for 9 hours under a hydrogen atmosphere.

After the catalyst in the reaction mixture was filtered off, the solvent was concentrated under reduced pressure to obtain the desired compound (6.89 g, 100%).

$^1$H-NMR (D$_2$O, 4.65 ppm) 3.23 (1H, dd, J=9.7 Hz, 6.4 Hz), 3.15 (2H, dd, J=7.7 Hz, 4.4 Hz), 1.99 (1H, tdd, J=6.4 Hz 12.7 Hz, 3.4 Hz), 1.72~1.80 (1H, m), 1.60~1.71 (1H, m), 1.47 (1H, dddd, J=12.7 Hz, 11.2 Hz, 9.7 Hz, 3.4 Hz).

EXAMPLE 20

Synthesis of (3S)-3-(N-methyl-benzyloxycarbonylamino)-2-piperidone

Tetrahydrofuran (15 mL) and 35% formalin (0.80 mL, 9.3240 mmol) were added to (3S)-3-amino-2-piperidone (720.2 mg, 6.3092 mmol), and the resulting mixture was stirred at room temperature for 2 hours.

After the reaction mixture was concentrated under reduced pressure, methanol (15 mL) and sodium borohydride (477.4 mg, 12.6196 mmol) were added thereto, and the resulting mixture was stirred under ice-cooling for 30 minutes. The reaction mixture was concentrated under reduced pressure, after which water (20 mL), tetrahydrofuran (5 mL), sodium hydrogencarbonate (1.06 g, 12.62 mmol) and benzyloxycarbonyl chloride (d=1.195, 1.3 mL, 9.11 mmol) were added thereto in that order, and the resulting mixture was stirred overnight at room temperature.

The reaction mixture was extracted with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (50 g, chloroform:ethyl acetate=2:1~1:1) column chromatography to obtain the desired compound (0.43 g, 26%).

$^1$H-NMR (CDCl$_3$, internal standard TMS) A-form 7.29-7.39 (5H, m), 6.10 (1H, brs), 5.11~5.19 (2H, m), 4.50 (1H, dd, J=6.3 Hz, 11.2 Hz), 3.36 (1H, td, J=11.7 Hz, 3.9 Hz), 3.27~3.33 (1H, m), 2.91 (3H, s), 2.03~2.12 (1H, m), 1.81~2.01 (3H, m). B-form 7.29~7.39 (5H, m), 6.07 (1H, brs), 5.13 (2H, s), 4.29~4.36 (1H, m), 3.20~3.26 (1H, m), 3.15 (1H, td, J=11.7 Hz, 3.9 Hz), 2.94 (3H, s), 2.03~2.12 (1H, m), 1.81~2.01 (3H, m) 1H-NMR (DMSO-D6, 2.49 ppm, 24° C.) 7.61and7.63 (1H, brs), 7.27~7.39 (5H, m), 5.06and5.04 (2H, s, and m), 4.33and4.23 (1H, dd, J=11.2 Hz, 6.8 Hz, and m), 3.02~3.18 (2H, m), 2.75and2.74 (3H, s), 1.65~1.96 (4H, m). 1H-NMR (DMSO-D6, 2.49 ppm, 80° C.) 7.27~7.41 (6H, m), 5.08and5.07 (2H, s, and m), 4.30 (1H, m), 3.06~3.16 (2H, m), 2.78 (3H, s), 1.68~1.97 (4H, m). MS (FAB+, NBA) m/z: 263 [M+H]$^+$.

EXAMPLE 21

Synthesis of (3S)-3-(N-methyl-benzyloxycarbonylamino)-1-diaminophosphinyl-2-piperidone A solution of (3S)-3-(N-methyl-benzyloxycarbonylamino)-2-piperidone (378.4 mg, 1.4426 mmol) in tetrahydrofuran (10 mL) was cooled at an external temperature of −78° C., after which an n-butyllithium-hexane solution (2.46 M, 0.56 mL, 1.3776 mmol) was slowly dropped thereinto and the resulting mixture was stirred at the same temperature for 30 minutes. Subsequently, a solution of phosphorus oxychloride (265.4 mg, 1.7309 mmol) in tetrahydrofuran (1 mL) was added thereto and stirred for 1 hour, and then a solution of ammonia in chloroform (1.7 M, 5.3 mL, 9.01 mmol) was added thereto and stirred for 5 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (40 g, chloroform:methanol=19:1~14:1~9:1) column chromatography to obtain the desired compound (310.9 mg, 63%).

$^1$H-NMR (CDCl$_3$, internal standard TMS) A-form 7.30-7.39 (5H, m), 5.14 (2H, s), 4.25~4.31 (1H, m), 3.84~3.92 (1H, m), 3.51~3.59 (1H, m), 3.33 (2H, br s), 3.27 (2H, brs), 2.97 (3H, s), 2.09~2.18 (1H, m), 1.96~2.09 (2H, m), 1.79~1.89 (1H, m). B-form 7.30-7.39 (5H, m), 5.08~5.20 (2H, m), 4.07~4.13 (1H, m), 3.80~3.89 (1H, m), 3.30~3.40 (1H, m), 3.22 (2H, br s), 3.00 (3H, s), 2.88 (2H, brs), 2.09~2.18 (1H, m), 1.96~2.09 (2H, m), 1.79~1.89 (1H, m). MS (FAB+, NBA) m/z: 341 [M+H]$^+$.

EXAMPLE 22

Synthesis of (3S)-3-methylamino-1-diaminophosphinyl-2-piperidone

Palladium black (20 mg) was added to a solution of (3S)-3-(N-methyl-benzyloxycarbonylamino)-1-diaminophosphinyl-2-piperidone (203.1 mg, 0.5968 mmol) in ethanol (4 mL), and the resulting mixture was stirred at room temperature for 24 hours under a hydrogen atmosphere.

After the catalyst in the reaction mixture was filtered off, the solvent was concentrated under reduced pressure to obtain the desired compound (122.0 mg, 99%).

$^1$H-NMR (D$_2$O, 4.65 ppm) 3.74 (1H, dd, J=12.2 Hz, 6.3 Hz), 3.46~3.53 (2H, m), 2.52 (3H, s), 2.20~2.28 (1H, m), 1.84~1.94 (1H, m), 1.68~1.83 (1H, m), 1.62 (1H, tdd, J=12.2 Hz, 9.8 Hz, 6.3 Hz). MS (FAB+, Gly) m/z: 207 [M+H]$^+$.

EXAMPLE 23

Synthesis of (3S)-3-(N-n-propyl-benzyloxycarbonylamino)-2-piperidone

In a mixture of methanol (3 mL) and toluene (3 mL) was dissolved (3S)-3-amino-2-piperidone (3.00 g, 26.28 mmol), followed by adding thereto n-propionaldehyde (d=0.805, 2.0 mL, 27.72 mmol), and the resulting mixture was stirred at room temperature for 1 hour.

Methanol (30 mL) and sodium cyanoborohydride (2.45 g, 38.99 mmol) were added to the reaction mixture, followed by stirring at room temperature for 30 minutes. Then, acetic acid (d=1.049, 1.7 mL, 29.70 mmol) was added to the reaction mixture and the resulting mixture was stirred at room temperature for 45 minutes.

The reaction mixture was concentrated under reduced pressure, after which water (50 mL), tetrahydrofuran (25 mL), sodium hydrogencarbonate (8.83 g, 105.11 mmol) and benzyloxycarbonyl chloride (d=1.195, 7.5 mL, 52.54 mmol) were added thereto in that order, and the resulting mixture was stirred overnight at room temperature.

Water was added to the reaction mixture, followed by extraction with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (150 g, chloroform:ethyl acetate=3:1~2:1~3:2~1:1) column chromatography to obtain the desired compound (0.56 g, 7%).

$^1$H-NMR (CDCl$_3$, internal standard TMS) A-form 7.23~7.39 (5H, m), 5.88 (1H, brs), 5.16 (2H, s), 3.83~3.93 (1H, m), 3.18~3.45 (4H, m), 2.17~2.27 (1H, m), 1.91~2.09 (2H, m), 1.77~1.88 (1H, m), 1.50~1.70 (2H, m), 0.88 (3H, t, J=7.3 Hz). B-form 7.23~7.39 (5H, m), 5.74 (1H, brs), 5.04~5.14 (2H, m), 3.70~3.82 (1H, m), 3.18~3.45 (2H, m), 3.07~3.14 (1H, m), 2.87~2.96 (1H, m), 2.00~2.10 (2H, m), 1.77~1.88 (1H, m), 1.50~1.77 (3H, m), 0.93 (3H, t, J=7.3 Hz). MS (FAB+, NBA) m/z: 291 [M+H]$^+$.

EXAMPLE 24

Synthesis of (3S)-3-(N-n-propyl-benzyloxycarbonylamino)-1-diaminophosphinyl-2-piperidone A solution of (3S)-3-(N-n-propyl-benzyloxycarbonylamino)-2-piperidone (383.3 mg, 1.3201 mmol) in tetrahydrofuran (5 mL) was cooled at an external temperature of −78° C., after which an n-butyllithium-hexane solution (2.46 M, 0.50 mL, 1.2300 mmol) was slowly dropped thereinto and the resulting mixture was stirred at the same temperature for 30 minutes. Subsequently, a solution of phosphorus oxychloride (242.9 mg, 1.5842 mmol) in tetrahydrofuran (2 mL) was added thereto and stirred for 2.5 hours, and then a solution of ammonia in chloroform (1.7 M, 5.4 mL, 9.18 mmol) was added thereto and stirred for 15 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (30 g, chloroform:methanol=19:1~14:1~9:1) column chromatography to obtain the desired compound (273.1 mg, 56%).

$^1$H-NMR (CDCl$_3$, internal standard TMS) A-form 7.29~7.40 (5H, m), 5.08~5.16 (2H, m), 3.91~3.98 (1H, m), 3.62~3.74 (1H, m), 3.51 (1H, td, J=12.2 Hz, 3.4 Hz), 3.33~3.46 (1H, m), 3.31 (2H, brs), 3.15~3.27 (1H, m), 3.19 (2H, brs), 2.08~2.20 (2H, m), 1.93~2.06 (1H, m), 1.54~1.80 (3H, m), 0.91 (3H, t, J=7.3 Hz). B-form 7.29~7.40 (5H, m), 5.03~5.19 (2H, m), 3.82~3.89 (1H, m), 3.62~3.74 (1H, m), 3.33~3.46 (1H, m), 3.15~3.27 (2H, m), 3.15 (2H, brs), 2.53 (2H, brs), 2.08~2.20 (2H, m), 1.93~2.06 (1H, m), 1.54~1.80 (3H, m), 0.95 (3H, t, J=7.3 Hz). MS (FAB+, Gly) m/z: 369 [M+H]$^+$, 737 [2M+H]$^+$.

EXAMPLE 25

Synthesis of (3S)-3-n-propylamino-1-diaminophosphinyl-2-piperidone

Palladium black (16 mg) was added to a solution of (3S)-3-(N-n-propyl-benzyloxycarbonylamino)-1-diaminophosphinyl-2-piperidone (160.6 mg, 0.4360 mmol) in ethanol (3 mL), and the resulting mixture was stirred at room temperature for 4 hours under a hydrogen atmosphere.

After the catalyst in the reaction mixture was filtered off, the solvent was concentrated under reduced pressure to obtain the desired compound (93.3 mg, 97%).

$^1$H-NMR (CD$_3$OD, 3.30 ppm) 3.59~3.64 (2H, m), 3.30 (1H, dd, J=11.7 Hz, 6.3 Hz), 2.60 (2H, t, J=7.3 Hz), 2.18~2.25 (1H, m), 1.89~1.99 (1H, m), 1.79~1.88 (1H, m), 1.50~1.62 (3H, m), 0.95 (3H, t, J=7.3 Hz). MS (FAB+, Gly) m/z: 235 [M+H]$^+$, 469 [2M+H]$^+$.

EXAMPLE 26

Synthesis of (3S)-3-(N-isopropyl-benzyloxycarbonylamino)-2-piperidone

Acetone (15 mL) was added to (3S)-3-amino-2-piperidone (3.00 g, 26.28 mmol) and the resulting mixture was stirred overnight at room temperature.

The reaction mixture was concentrated under reduced pressure to obtain a colorless oil (3.94 g, 97%).

Methanol (30 mL) and sodium cyanoborohydride (1.31 g, 20.85 mmol) were added to the obtained colorless oil (3.20 g, 20.75 mmol), followed by stirring at room temperature for 30 minutes. Then, acetic acid (d=1.049, 1.31 mL, 22.88 mmol) was added to the reaction mixture and the resulting mixture was stirred at room temperature for 30 minutes.

The reaction mixture was concentrated under reduced pressure, after which water (50 mL), tetrahydrofuran (30 mL), sodium hydrogencarbonate (6.97 g, 82.97 mmol) and benzyloxycarbonyl chloride (d=1.195, 11.8 mL, 82.66 mmol) were added thereto in that order, and the resulting mixture was stirred overnight at room temperature.

The organic layer of the reaction mixture was concentrated under reduced pressure and then extracted with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (50 g, chloroform:ethyl acetate=2:1~1:1) column chromatography to obtain the desired compound (0.69 g, 11%).

$^1$H-NMR (CDCl$_3$, internal standard TMS) A-form 7.28~7.38 (5H, m), 5.86 (1H, brs), 5.14 (2H, d, J=2.4 Hz)or4.99~5.13 (2H, m), 4.30~4.38 (1H, m), 3.61~3.68 (1H, m), 3.46 (1H, td, J=11.7 Hz, 3.4 Hz), 3.24~3.29 (1H, m), 2.29~2.39 (1H, m), 1.74~1.95 (3H, m), 1.25 (3H, d, J=6.8 Hz), 1.15 (3H, d, J=6.8 Hz). B-form 7.28~7.38 (5H, m), 5.68 (1H, brs), 4.99~5.13 (2H, m) or5.11 (2H, d, J=2.4 Hz), 4.46~4.54 (1H, m), 3.52~3.60 (1H, m), 3.03~3.07 (1H, m), 2.78 (1H, td, J=11.7 Hz, 3.4 Hz), 2.04~2.15 (1H, m), 1.67~1.95 (3H, m), 1.25 (3H, d, J=6.8 Hz), 1.14 (3H, d, J=6.8 Hz). MS (FAB+, NBA) m/z: 291 [M+H]$^+$.

EXAMPLE 27

Synthesis of (3S)-3-(N-isopropyl-benzyloxycarbonylamino)-1-diaminophosphinyl-2-piperidone A solution of (3S)-3-(N-isopropyl-benzyloxycarbonylamino)-2-piperidone (783.0 mg, 2.6967 mmol) in tetrahydrofuran (15 mL) was cooled at an external temperature of −78° C., after which an n-butyllithium-hexane solution (2.46 M, 1.04 mL, 2.5584 mmol) was added dropwise thereto over a period of 10 minutes, and the resulting mixture was stirred at the same temperature for 30 minutes. Subsequently, a solution of phosphorus oxychloride (500.0 mg, 3.2609 mmol) in tetrahydrofuran (3 mL) was added thereto and stirred for 30 minutes, and then a solution of ammonia in chloroform (1.7 M, 11.1 mL, 18.87 mmol) was added thereto and stirred for 5 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (50 g, chloroform:methanol=19:1~14:1~9:1) column chromatography to obtain the desired compound (756.2 mg, 76%).

$^1$H-NMR (CDCl$_3$, internal standard TMS) A-form 7.30~7.40 (5H, m), 5.08~5.14 (2H, m), 4.36~4.45 (1H, m), 3.94~4.00 (1H, m), 3.56~3.61 (1H, m), 3.49 (1H, td, J=12.7 Hz, 3.4 Hz), 3.35 (2H, brs) 3.18 (2H, brs), 2.14~2.25 (1H, m), 1.92~2.05 (2H, m), 1.68~1.80 (1H, m), 1.24 (3H, d, J=6.8 Hz), 1.16 (3H, d, J=6.8 Hz). B-form 7.30~7.40 (5H, m), 5.04~5.16 (2H, m), 4.54~4.64 (1H, m), 3.83~3.90 (1H, m), 3.56~3.61 (1H, m), 3.18 (2H, brs), 3.14 (1H, td, J=12.7 Hz, 3.4 Hz), 2.48 (2H, brs), 2.14~2.25 (1H, m), 1.92~2.05 (2H, m), 1.68~1.80 (1H, m), 1.22 (3H, d, J=6.8 Hz), 1.16 (3H, d, J=6.8 Hz). MS (FAB+, NBA) m/z: 369 [M+H]$^+$.

EXAMPLE 28

Synthesis of (3S)-3-isopropylamino-1-diaminophosphinyl-2-piperidone

Palladium black (45 mg) was added to a solution of (3S)-3-(N-isopropyl-benzyloxycarbonyl-amino)-1-diaminophosphinyl-2-piperidone (450.1 mg, 1.2219 mmol) in ethanol (9 mL), and the resulting mixture was stirred at room temperature for 24 hours under a hydrogen atmosphere.

The catalyst in the reaction mixture was filtered off and the solvent was concentrated under reduced pressure to obtain the desired compound (284.6 mg, 99%).

$^1$H-NMR (D$_2$O, 4.65 ppm) 3.68 (1H, dd, J=11.2 Hz, 6.8 Hz), 3.42~3.58 (2H, m), 3.08~3.17 (1H, m), 2.15~2.23 (1H, m), 1.74~1.89 (2H, m), 1.48~1.58 (1H, m), 1.06 (6H, d, J=6.3 Hz). MS (FAB+, Gly) m/z: 235 [M+H]$^+$.

EXAMPLE 29

Synthesis of (3S)-3-(N-n-butyl-benzyloxycarbonylamino)-2-piperidone

To a solution of (3S)-3-amino-2-piperidone (1.51 g, 13.23 mmol) in methanol (3 mL) was added n-butyraldehyde (d=0.800, 1.3 mL, 14.42 mmol), and the resulting mixture was stirred at room temperature for 3.5 hours.

After the reaction mixture was concentrated under reduced pressure, methanol (12 mL) and sodium cyanoborohydride (2.45 g, 38.99 mmol) were added thereto, followed by stirring at room temperature for 30 minutes. Then, acetic acid (d=1.049, 0.84 mL, 14.67 mmol) was added to the reaction mixture and the resulting mixture was stirred at room temperature for 30 minutes.

After the reaction mixture was concentrated under reduced pressure, water and sodium hydrogencarbonate (2.50 g, 29.75 mmol) were added thereto, followed by extraction with ethyl acetate. The ethyl acetate solution was washed with a saturated aqueous sodium chloride solution and dried over anhydrous sodium sulfate, and then the solvent was concentrated under reduced pressure. To the oil thus obtained was added chloroform (50 mL), followed by adding thereto triethylamine (d=0.7225, 2.8 mL, 20.00 mmol) and then benzyloxycarbonyl chloride (d=1.195, 2.8 mL, 19.61 mmol) under ice-cooling, and the resulting mixture was stirred at the same temperature for 1 hour.

Water was added to the reaction mixture, followed by extraction with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (50 g, chloroform:ethyl acetate=3:1~2:1~1:1) column chromatography to obtain the desired compound (0.38 g, 9%).

$^1$H-NMR (CDCl$_3$, internal standard TMS) A-form 7.27~7.38 (5H, m), 5.84 (1H, brs), 5.16 (2H, s), 3.83~3.92 (1H, m), 3.23~3.46 (4H, m), 2.19~2.27 (1H, m), 2.01~2.09 (1H, m), 1.91~2.00 (1H, m), 1.78~1.87 (1H, m), 1.42~1.65 (2H, m), 1.25~1.36 (2H, m), 0.88 (3H, t, J=7.3 Hz). B-form 7.27~7.38 (5H, m), 5.69 (1H, brs)5.06~5.16 (2H, m), 3.72~3.83 (1H, m), 3.23~3.40 (2H, m), 3.08~3.15 (1H, m), 2.88~2.97 (1H, m), 1.67~2.10 (4H, m), 1.42~1.65 (2H, m), 1.32~1.45 (2H, m), 0.94 (3H, t, J=7.3 Hz). MS (FAB+, NBA) m/z: 305 [M+H]$^+$.

EXAMPLE 30

Synthesis of (3S)-3-(N-n-butyl-benzyloxycarbonylamino)-1-diaminophosphinyl-2-piperidone A solution of (3S)-3-(N-n-butyl-benzyloxycarbonylamino)-2-piperidone (403.2 mg, 1.3246 mmol) in tetrahydrofuran (12 mL) was cooled at an external temperature of −78° C., after which an n-butyllithium-hexane solution (2.46 M, 0.51 mL, 1.2546 mmol) was slowly dropped thereinto, and the resulting mixture was stirred at the same temperature for 1.5 hours. Subsequently, a solution of phosphorus oxychloride (243.7 mg, 1.5894 mmol) in tetrahydrofuran (1 mL) was added thereto and stirred for 30 minutes, and then a solution of ammonia in chloroform (1.7 M, 5.0 mL, 8.50 mmol) was added thereto and stirred for 5 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (30 g, chloroform:methanol=14:1~9:1) column chromatography to obtain the desired compound (185.0 mg, 37%).

$^1$H-NMR (CDCl$_3$, internal standard TMS) A-form 7.29~7.40 (5H, m), 5.07~5.15 (2H, m), 3.90~3.98 (1H, m), 3.62~3.74 (1H, m), 3.51 (1H, td, J=12.2 Hz, 3.4 Hz), 3.33~3.47 (1H, m), 3.32 (2H, brs), 3.15~3.30 (1H, m), 3.18 (2H, brs), 2.07~2.20 (2H, m), 1.95~2.05 (1H, m), 1.50~1.80 (3H, m), 1.27~1.42 (2H, m), 0.90 (3H, t, J=7.3 Hz) B-form 7.29~7.40 (5H, m), 5.03~5.18 (2H, m), 3.82~3.90 (1H, m), 3.62~3.74 (1H, m), 3.33~3.47 (1H, m), 3.15~3.30 (2H, m), 3.16 (2H, brs), 2.54 (2H, brs), 2.07~2.20 (2H, m), 1.95~2.05 (1H, m), 1.50~1.80 (3H, m), 1.27~1.42 (2H, m), 0.95 (3H, t, J=7.3 Hz). MS (FAB+, Gly) m/z: 383 [M+H]$^+$, 765 [2M+H]$^+$.

EXAMPLE 31

Synthesis of (3S)-3-n-butylamino-1-diaminophosphinyl-2-piperidone

In a mixture of ethanol (6 mL) and water (0.3 mL) was dissolved (3S)-3-(N-n-butyl-benzyloxycarbonylamino)-1-diaminophosphinyl-2-piperidone (126.5 mg, 0.3308 mmol), followed by adding thereto palladium black (13 mg), and the resulting mixture was stirred at room temperature for 6 hours under a hydrogen atmosphere.

The catalyst in the reaction mixture was filtered off and the solvent was concentrated under reduced pressure, followed by purification using Diaion HP-20 (10 mL; elution with a water-methanol gradient), whereby the desired compound (19.2 mg, 23%) was obtained.

$^1$H-NMR (CD$_3$OD, 3.30 ppm) 3.59~3.64 (2H, m), 3.31 (1H, dd, J=11.2 Hz, 6.8 Hz), 2.64 (2H, dd, J=7.8 Hz, 6.8 Hz)2.18~2.25 (1H, m), 1.89~1.99 (1H, m), 1.78~1.88 (1H, m), 1.48~1.65 (3H, m), 1.34~1.43 (2H, m), 0.94 (3H, t, J=7.3 Hz). MS (FAB+, Gly) m/z: 249 [M+H]$^+$, 497 [2M+H]$^+$.

EXAMPLE 32

Synthesis of (3S)-3-(N-benzyl-benzyloxycarbonylamino)-2-piperidone

Benzaldehyde (d=1.044, 5.4 mL, 53.12 mmol) was added to (3S)-3-amino-2-piperidone (4.00 g, 35.04 mmol), and the resulting mixture was stirred at room temperature for 5 minutes.

Toluene (10 mL) and ether (20 mL) were added to the crystallized reaction mixture, followed by decantation, and the crystals were washed with ether and an ether-n-hexane mixture to obtain (3S)-3-benzylideneamino-2-piperidone (5.78 g). On the other hand, the solution obtained by decantation and the washings were concentrated together under reduced pressure and the resulting crystals were washed with an ether-n-hexane mixture to obtain (3S)-3-benzylideneamino-2-piperidone (1.00 g) (total 6.78 g, 96%).

Sodium cyanoborohydride (1.64 g, 26.10 mmol) was added to a solution of (3S)-3-benzylideneamino-2-piperidone (5.26 g, 26.01 mmol) in methanol (60 mL) under ice-cooling, and the resulting mixture was stirred at the same temperature for 30 minutes. Then, acetic acid (d=1.049, 1.80 mL, 31.21 mmol) was added to the reaction mixture, followed by stirring under ice-cooling for 30 minutes.

After the reaction mixture was concentrated under reduced pressure, water (100 mL) and tetrahydrofuran (50 mL) were added thereto, followed by adding thereto sodium hydrogencarbonate (8.74 g, 104.04 mmol) and benzyloxycarbonyl chloride (d=1.195, 9.3 mL, 65.14 mmol) under ice-cooling, and the resulting mixture was stirred under ice-cooling for 40 minutes and then at room temperature for 20 minutes.

Water was added to the reaction mixture, followed by extraction with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (100 g, chloroform:ethyl acetate=2:1 to 1:1~chloroform:ethyl acetate:methanol=1:1:0.1) column chromatography to obtain the desired compound (7.20 g, 79%).

$^1$H-NMR (CDCl$_3$, internal standard TMS) A-form 7.24~7.39 (10H, m), 5.98 (1H, brs), 5.17 (2H, s), 4.69 (1H, d, J=16.1 Hz), 4.53 (1H, d, J=16.1 Hz), 3.93~4.02 (1H, m), 3.35 (1H, td, J=11.7 Hz, 3.4 Hz), 3.21~3.26 (1H, m), 2.03~2.14 (1H, m), 1.78~1.86 (1H, m), 1.50~1.72 (2H, m). B-form 7.24~7.39 (10H, m), 5.81 (1H, brs), 5.11~5.21 (2H, m), 4.84 (1H, d, J=15.1 Hz), 4.48 (1H, d, J=15.1 Hz), 3.70~3.78 (1H, m), 3.02~3.08 (1H, m), 2.85 (1H, td, J=11.7 Hz, 3.4 Hz), 1.86~1.97 (1H, m), 1.78~1.86 (1H, m), 1.50~1.72 (2H, m). MS (FAB+, NBA) m/z: 339 [M+H]$^+$.

EXAMPLE 33

Synthesis of (3S)-3-(N-benzyl-benzyloxycarbonylamino)-1-diaminophosphinyl-2-piperidone A solution of (3S)-3-(N-benzyl-benzyloxycarbonylamino)-2-piperidone (6.90 g, 20.39 mmol) in tetrahydrofuran (100 mL) was cooled at an external temperature of −78° C., after which an n-butyllithium-hexane solution (2.46 M, 7.9 mL, 19.43 mmol) was added dropwise thereto over a period of 20 minutes, and the resulting mixture was stirred at the same temperature for 20 minutes. Subsequently, a solution of phosphorus oxychloride (3.75 g, 24.46 mmol) in tetrahydrofuran (10 mL) was added thereto and the resulting mixture was stirred at the same temperature for 10 minutes and then at room temperature for 20 minutes. This mixture was cooled at an external temperature of −78° C. and then liquid ammonia (d=0.771, 2.5 mL, 113.18 mmol) was added thereto and stirred for 5 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (120 g, chloroform ethyl acetate:methanol=10:10:0~10:9:1~10:8:2) column chromatography to obtain the desired compound (4.17 g, 49%).

$^1$H-NMR (CDCl$_3$, internal standard TMS) A-form 7.27~7.39 (10H, m), 5.13~5.20 (2H, m), 4.76 (1H, brd, J=15.6 Hz), 4.48 (1H, brd, J=15.6 Hz), 3.85~3.92 (1H, m), 3.72~3.81 (1H, m), 3.47 (1H, td, 12.2 Hz, 3.4 Hz), 3.31 (2H, brs), 3.20 (2H, brs), 1.95~2.12 (1H, m), 1.78~1.94 (2H, m), 1.54~1.72 (1H, m). B-form 7.27~7.39 (10H, m), 5.11~5.26 (2H, m), 4.94 (1H, brd, J=15.6 Hz), 4.42 (1H, brd, J=15.6 Hz), 3.72~3.81 (1H, m), 3.61~3.68 (1H, m), 3.11~3.20 (1H, m), 3.14 (2H, brs), 2.54 (2H, brs), 1.95~2.12 (1H, m), 1.78~1.94 (2H, m), 1.54~1.72 (1H, m). MS (FAB+, NBA) m/z: 417 [M+H]$^+$.

EXAMPLE 34

Synthesis of (3S)-3-benzylamino-1-diaminophosphinyl-2-piperidone

In ethanol (10 mL) was dissolved (3S)-3-(N-benzyl-benzyloxycarbonylamino)-1-diaminophosphinyl-2-piperidone (501.1 mg, 1.2034 mmol), followed by adding thereto palladium black (50 mg), and the resulting mixture was stirred overnight at room temperature under a hydrogen atmosphere.

The catalyst in the reaction mixture was filtered off and the solvent was concentrated under reduced pressure, followed by purification using Dianion HP-20 (25 mL; elution with a water-methanol gradient), whereby the desired compound (251.1 mg, 74%) was obtained.

$^1$H-NMR (CD$_3$OD, 3.30 ppm) 7.30~7.37 (4H, m), 7.25 (1H, tt, J=6.8 Hz, 2.0 Hz), 3.83 (2H, q, J=12.7 Hz), 3.60 (2H, ddd, J=7.3 Hz, 4.3 Hz, 1.5 Hz), 3.28 (1H, dd, J=11.2 Hz, 6.8 Hz), 2.23 (1H, td, J=11.2 Hz, 5.9 Hz), 1.89~1.99 (1H, m), 1.75~1.86 (1H, m), 1.61 (1H, dddd, J=12.7 Hz, 11.2 Hz, 9.8 Hz, 5.9 Hz) MS (FAB+, Gly) m/z: 283 [M+H]$^+$.

EXAMPLE 35

Synthesis of (3S)-3-(N-furfuryl-benzyloxycarbonylamino)-2-piperidone

Furfural (d=1.160, 0.91 mL, 10.99 mmol) was added to a solution of (3S)-3-amino-2-piperidone (1.15 g, 10.07 mmol) in methanol (5 mL), and the resulting mixture was stirred overnight at room temperature.

After the reaction mixture was concentrated under reduced pressure, methanol (10 mL) and sodium borohydride (0.46 g, 12.16 mmol) were added thereto, and the resulting mixture was stirred at room temperature for 3 hours.

The reaction mixture was concentrated under reduced pressure, after which chloroform (15 mL) was added thereto, followed by adding thereto triethylamine (d=0.7255, 2.8 mL, 19.99 mmol) and benzyloxycarbonyl chloride (d=1.195, 2.2 mL, 12.16 mmol) under ice-cooling, and the resulting mixture was stirred under ice-cooling for 2 hours.

Water was added to the reaction mixture, followed by extraction with ethyl acetate. The ethyl acetate solution was washed with a saturated aqueous sodium chloride solution and dried over anhydrous sodium sulfate, and then the solvent was concentrated under reduced pressure. The oil thus obtained was purified by a silica gel (100 g, chloroform: ethyl acetate=2:1 to 1:1~chloroform:ethyl acetate:methanol=1:1:0.1) column chromatography to obtain the desired compound (7.20 g, 79%).

$^1$H-NMR (CDCl$_3$, internal standard TMS) A-form 7.27~7.37 (6H, m), 6.30 (1H, dd, J=2.9 Hz, 2.0 Hz), 6.18 (1H, d, J=2.9 Hz), 5.94 (1H, brs), 5.17 (2H, s), 4.65 (1H, brd, J=16.1 Hz), 4.49 (1H, brd, J=16.1 Hz), 4.05~4.13 (1H, m), 3.37 (1H, td, J=11.7 Hz, 3.4 Hz), 3.22~3.28 (1H, m), 2.01~2.11 (1H, m), 1.58~1.95 (3H, m). B-form 7.27~7.37 (6H, m), 6.31~6.34 (2H, m), 5.79 (1H, brs), 5.09~5.17 (2H, m), 4.82 (1H, brd, J=15.1 Hz), 4.45 (1H, brd, J=15.1 Hz), 3.87~3.95 (1H, m), 3.06~3.12 (1H, m), 2.89 (1H, td, J=11.7 Hz, 3.4 Hz), 1.58~1.95 (4H, m). MS (FAB+, NBA) m/z: 329 [M+H]$^+$.

EXAMPLE 36

Synthesis of (3S)-3-(N-furfuryl-benzyloxycarbonylamino)-1-diaminophosphinyl-2-piperidone A solution of (3S)-3-(N-furfuryl-benzyloxycarbonylamino)-2-piperidone (1.11 g, 3.38 mmol) in tetrahydrofuran (25 mL) was cooled at an external temperature of −78° C., after which an n-butyllithium-hexane solution (2.46 M, 1.3 mL, 3.20 mmol) was added dropwise thereto over a period of 20 minutes, and the resulting mixture was stirred at the same temperature for 20 minutes. Subsequently, a solution of phosphorus oxychloride (0.62 g, 4.04 mmol) in tetrahydrofuran (3 mL) was added thereto and the resulting mixture was stirred at the same temperature for 1 hour and then at room temperature for 45 minutes. This mixture was cooled at an external temperature of −78° C. and then a solution of ammonia in chloroform (1.7 M, 21 mL, 35.7 mmol) was added thereto and stirred for 5 minutes.

An aqueous sodium chloride solution was added to the reaction mixture, followed by extraction with chloroform. The chloroform solution was washed with a saturated aqueous sodium chloride solution and dried over anhydrous sodium sulfate, and then the solvent was concentrated under reduced pressure. The oil thus obtained was purified by a silica gel (50 g, chloroform:methanol=19:1~14:1) column chromatography to obtain the desired compound (0.61 g, 45%).

$^1$H-NMR (CDCl$_3$, internal standard TMS) A-form 7.32~7.39 (6H, m), 6.32 (1H, dd, J=4.9 Hz, 3.0 Hz), 6.23 (1H, d, J=3.0 Hz), 5.12~5.20 (2H, m), 4.72 (1H, brd, J=16.1 Hz), 4.42 (1H, brd, J=16.1 Hz), 3.87~3.95 (2H, m), 3.48 (1H, td, J=12.2 Hz, 3.4 Hz), 3.31 (2H, brs), 3.20 (2H, brs), 1.64~2.10 (4H, m). B-form 7.32~7.39 (6H, m), 6.33~6.35 (2H, m), 5.07~5.23 (2H, m), 4.91 (1H, brd, J=16.1 Hz), 4.38 (1H, brd, J=16.1 Hz), 3.77~3.87 (2H, m), 3.16 (2H, brs), 3.13~3.23 (1H, m), 2.58 (2H, brs), 1.64~2.10 (4H, m). MS (FAB+, NBA) m/z: 407 [M+H]$^+$.

EXAMPLE 37

Synthesis of (3S)-3-furfurylamino-1-diaminophosphinyl-2-piperidone

In ethanol (6 mL) was dissolved (3S)-3-(N-furfuryl-benzyloxycarbonylamino)-1-diaminophosphinyl-2-piperidone (356.2 mg, 0.8765 mmol), followed by adding thereto palladium black (35 mg), and the resulting mixture was stirred overnight at room temperature under a hydrogen atmosphere.

The catalyst in the reaction mixture was filtered off and the solvent was concentrated under reduced pressure, followed by purification using Dianion HP-20 (20 mL; elution with a water-methanol gradient), whereby the desired compound (78.4 mg, 33%) was obtained.

$^1$H-NMR (CD$_3$OD, 3.30 ppm) 7.44 ($^1$H, dd, J=2.0 Hz, 1.0 Hz), 6.35 (1H, dd, J=3.4 Hz, 2.0 Hz), 6.29 (1H, dd, J=3.4 Hz, 1.0 Hz), 3.80~3.89 (2H, m), 3.60 (1H, t, J=6.3 Hz), 3.59 (1H, t, J=6.3 Hz), 3.26 (1H, dd, J=11.2 Hz, 6.8 Hz), 2.17~2.25 (1H, m), 1.88~1.98 (1H, m), 1.75~1.86 (1H, m), 1.56 (1H, dddd, J=12.7 Hz, 11.2 Hz, 9.8 Hz, 5.9 Hz). MS (FAB+, Gly) m/z: 273 [M+H]$^+$.

EXAMPLE 38

Synthesis of (3S, P (RS))-3-benzyloxycarbonylamino-1-amino(benzoylamino)phosphinyl-2-piperidone Benzoyl chloride (281 mg, 2.0 mmol) was added dropwise to a suspension of (3S)-3-benzyloxycarbonylamino-1-diaminophosphinyl-2-piperidone (475 mg, 1.5 mmol) in pyridine (10 mL) at room temperature and stirred at the same temperature for 8 hours.

The reaction mixture was concentrated under reduced pressure while being heated at about 50° C., and the resulting residue was purified by a silica gel (ethyl acetate:methanol=40:1~30:1) column chromatography and then crystallized from hexane-ethyl acetate (1:1). The crystals obtained were filtered and then washed with the above-mentioned mixed solvent to obtain the desired compound (190 mg, 29%).

$^1$H-NMR (DMSO-D$_6$, internal standard TMS) 9.72 (1H, t, J=10.0 Hz), 7.90 (2H, dd, J=7.0 Hz, 1.7 Hz), 7.40~7.60 (4H, m), 7.30 (5H, m), 5.00 (2H, s), 4.74 (2H, brt, 4.0 Hz), 3.80~4.20 (2H, m), 3.65 (1H, m), 1.50~2.10 (4H, m). MS (FAB+) m/z: 431 [M+H]$^+$.

EXAMPLE 39

Synthesis of (3S, P (RS))-3-amino-1-amino(benzoylamino)phosphinyl-2-piperidone

Palladium black (12.1 mg) was added to a solution of (3S, P (RS))-3-benzyloxycarbonylamino-1-amino(benzoylamino)phosphinyl-2-piperidone (60.5 mg, 0.14 mmol) in ethanol (10 mL), and the resulting mixture was stirred at room temperature for 24 hours under a hydrogen atmosphere.

The reaction mixture was filtered by the use of Celite and the filtrate was concentrated under reduced pressure to obtain the desired compound (40.5 mg, 100%).

$^1$H-NMR (DMSO-D$_6$, internal standard TMS) 7.90 (2H, m), 7.40~7.60 (3H, m), 4.72 (2H, brs), 4.38 (1H, brs), 3.80 (1H, m), 3.60 (2H, m), 2.03 (1H, m), 1.78 (2H, m), 1.40 (1H, m). MS (FAB+) m/z: 297 [M+H]$^+$.

EXAMPLE 40

Synthesis of (3S, P (RS))-3-benzyloxycarbonylamino-1-amino(phenylcarbamoylamino)phosphinyl-2-piperidone Phenyl isocyanate (0.50 mL, 548 mg, 4.6 mmol) was added dropwise to a suspension of (3S)-3-benzyloxycarbonylamino-1-diaminophosphinyl-2-piperidone (1000 mg, 3.1 mmol) in pyridine (10 mL) at room temperature and stirred at the same temperature for 4 days.

The reaction mixture was concentrated under reduced pressure while being heated at about 50° C., and the resulting residue was purified by a silica gel (ethyl acetate:methanol=10:1) column chromatography to obtain the desired compound (500 mg, 36%).

$^1$H-NMR (DMSO-D$_6$, internal standard TMS) 8.78 (1H, s), 7.90 (1H, d, J=9.2 Hz), 7.49 (1H, d, J=9.2 Hz), 7.20~7.43 (9H, m), 6.95~7.05 (1H, m), 5.02 (2H, s), 4.78 (2H, brs), 3.30~3.80 (3H, m), 1.60~2.10 (4H, m). MS (ESI+) m/Z: 446 [M+H]$^+$.

EXAMPLE 41

Synthesis of (3S, P (RS))-3-amino-1-amino(phenylcarbamoylamino)phosphinyl-2-piperidone Palladium black (5 mg) was added to a solution of (3S)-3-benzyloxycarbonylamino-1-amino(phenylcarbamoylamino)phosphinyl-2-piperidone (30 mg, 0.067 mmol) in ethanol (10 mL), and the resulting mixture was stirred at room temperature for 24 hours under a hydrogen atmosphere.

The reaction mixture was filtered by the use of Celite and the filtrate was concentrated under reduced pressure to obtain the desired compound (20 mg, 96%).

$^1$H-NMR (DMSO-D$_6$, internal standard TMS) 8.88 (1H, s), 7.20~7.42 (4H, m), 6.98 (1H, t, J=7.1 Hz), 4.76 (2H, brs), 3.00~3.80 (6H, m), 1.93~2.13 (1H, m), 1.67~1.84 (2H, m), 1.30~1.55 (1H, m). MS (ESI+) m/z: 312 [M+H]$^+$.

EXAMPLE 42

Synthesis of (3R)-3-amino-1-diaminophosphinyl-2-piperidone

In ethanol (30 mL) was dissolved (3R)-3-benzyloxycarbonylamino-1-diaminophosphinyl-2-piperidone (804.9 mg, 2.4668 mmol), followed by adding thereto palladium black (80 mg), and the resulting mixture was stirred under a hydrogen atmosphere at an external temperature of 50° C. for 1 hour and then at room temperature overnight.

The catalyst in the reaction mixture was filtered off and the solvent was concentrated under reduced pressure to obtain the desired compound (464.0 mg, 98%).

$^1$H-NMR (D$_2$O, 4.65 ppm) 3.45 (1H, t, J=6.3 Hz), 3.44 (1H, t, J=6.3 Hz), 3.38 (1H, dd, J=11.2 Hz, 6.8 Hz), 2.00~2.09 (1H, m), 1.68~1.82 (2H, m), 1.39~1.49 (1H, m). MS (FAB+, Gly) m/z: 193 [M+H]+.

EXAMPLE 43

Synthesis of (3S)-3-amino-1-diaminophosphinyl-2-perhydroazepinone

In ethanol (10 mL) was dissolved (3S)-3-benzyloxycarbonylamino-1-diaminophosphinyl-2-perhydroazepinone (240.8 mg, 0.7765 mmol), followed by adding thereto palladium black (24 mg), and the resulting mixture was stirred overnight at room temperature under a hydrogen atmosphere.

The catalyst in the reaction mixture was filtered off and the solvent was concentrated under reduced pressure. The crystals thus obtained were washed with ether to obtain the desired compound (155.5 mg, 97%).

$^1$H-NMR (D$_2$O, 4.65 ppm) 3.85~3.93 (1H, m), 3.80 (1H, brd, J=10.3 Hz), 3.27 (1H, td, J=11.7 Hz, 15.6 Hz), 1.68~1.80 (3H, m), 1.55~1.66 (1H, m), 1.39~1.49 (1H, m), 1.21~1.33 (1H, m). MS (FAB+, Gly) m/z: 207 [M+H]$^+$, 413 [2M+H]$^+$.

EXAMPLE 44

Synthesis of (3S)-3-amino-1-diaminophosphinyl-2-pyrrolidone

In a mixture of ethanol (4 mL) and water (0.8 mL) was suspended (3S)-3-benzyloxycarbonylamino-1-diaminophosphinyl-2-pyrrolidone (401.5 mg, 1.2858 mmol), followed by adding thereto palladium black (40 mg), and the resulting mixture was stirred at room temperature for 5 hours under a hydrogen atmosphere.

The catalyst in the reaction mixture was filtered off and the solvent was concentrated under reduced pressure. The oil thus obtained was crystallized from an ethanol-ether mixed solvent to obtain the desired compound (132.5 mg, 54%).

$^1$H-NMR (D$_2$O, 4.65 ppm) 3.71 (1H, dd, J=11.2 Hz, 8.3 Hz), 3.57~3.63 (1H, m), 3.45 (1H, td, J=10.3 Hz, 6.4 Hz), 2.32~2.40 (1H, m), 1.72~1.83 (1H, m). MS (FAB+, Gly) m/z: 179 [M+H]$^+$.

EXAMPLE 45

Synthesis of (3S)-3-amino-1-diaminophosphinyl-2-piperidone hydrochloride (hydrochloride of the compound of Example 1)

In a mixture of methanol (16 mL) and water (4 mL) was dissolved (3S)-3-benzyloxycarbonylamino-1-diaminophosphinyl-2-piperidone (1.22 g, 3.74 mmol), followed by adding thereto palladium black (0.12 g), and the resulting mixture was stirred at room temperature for 4 hours under a hydrogen atmosphere.

The catalyst in the reaction mixture was filtered off and the solvent was concentrated under reduced pressure. The residue was dissolved in ethanol (25 mL)-ether (about 10 mL), followed by adding dropwise thereto a solution obtained by diluting a 4N hydrochloric acid-dioxane solution (0.9 mL) with ethanol (6 mL), and the crystals precipitated were collected by filtration to obtain the desired compound (0.69 g, 81%).

$^1$H-NMR (D$_2$O, 4.65 ppm) 3.83 (1H, dd, J=11.7 Hz, 6.8 Hz), 3.47~3.53 (2H, m), 2.19 (1H, td, J=11.7 Hz, 6.8 Hz), 1.74~1.92 (2H, m), 1.59~1.72 (1H, m).

EXAMPLE 46

Synthesis of (3S)-3-amino-1-diaminophosphinyl-2-piperidone ½ dibenzoyl-D-(−)-tartrate (½ dibenzoyl-D-(−)-tartrate of the compound of Example 1)

In ethanol (50 mL) was suspended (3S)-3-benzyloxycarbonylamino-1-diaminophosphinyl-2-piperidone (5.0 g, 15.3 mmol), followed by adding thereto palladium black (250 mg), and the resulting mixture was stirred at room temperature for 1 day under a hydrogen atmosphere. The catalyst in the reaction mixture was filtered off and water (10 mL) and a solution of dibenzoyl-D-(−)-tartaric acid (2.88 g, 7.7 mmol) in ethanol (40 mL) were added to the filtrate obtained, followed by adding thereto ethanol (40 mL). The crystals precipitated were collected by filtration to obtain the desired compound (4.77 g, 84%). The crystals were not observed to have hygroscopicity which the compounds of Example 1 and Example 45 had, indicating that the crystals were excellent in stability.

$^1$H-NMR (CD$_3$OD, internal standard TMS) 8.12~8.23 (2H, m), 7.55~7.65 (1H, m), 7.42~7.53 (2H, m), 5.84 (1H, s), 3.80~3.99 (1H, m), 3.53~3.68 (2H, m), 2.15~2.37 (1H, m), 1.64~1.95 (3H, m). MS (ESI+) m/z: 193 [M+H]$^+$. MS (ESI−) m/z: 357 [M (dibenzoyltartaric acid)-H]$^−$.

EXAMPLE 47

Synthesis of (3S, P (R or S))-3-benzyloxycarbonylamino-1-amino(acetylamino)phosphinyl-2-piperidone and (3S, P (S or R))-3-benzyloxycarbonyl-amino-1-amino(acetylamino)phosphinyl-2-piperidone At room temperature, acetyl chloride (0.52 mL, 7.31 mmol) was added dropwise to a solution obtained by dissolving (3S)-3-benzyloxycarbonylamino-2-piperidone (2.00 g, 6.13 mmol) in pyridine (80 mL) with heating, and the resulting mixture was stirred at the same temperature for 6 hours.

The reaction mixture was concentrated under reduced pressure and to the resulting residue was added a 30% aqueous acetone solution, after which the crystals precipitated were collected by filtration. Acetone was added to the crystals obtained and the insoluble material was filtered off, after which the filtrate was concentrated and the crystals were washed with an ethyl acetate-ether mixed solvent to obtain the desired compound (3S, P (S or R))-3-benzyloxycarbonyl-amino-1-amino(acetylamino)phosphinyl-2-piperidone (0.41 g, 18%).

On the other hand, the 30% aqueous acetone solution freed from the crystals was purified by the use of Dianion HP-20 (100 mL; elution with a water-acetone gradient). After the eluate was concentrated, the resulting crystals were dissolved in ethyl acetate and the insoluble material was filtered off. The filtrate was concentrated and the crystals thus obtained were washed with ether to obtain the desired compound (3S, P (R or S))-3-benzyloxycarbonylamino-1-amino(acetylamino)phosphinyl-2-piperidone (0.72 g, 32%).

(3S, P (R or S))-3-benzyloxycarbonylamino-1-amino(acetylamino)phosphinyl-2-piperidone $^1$H-NMR (DMSO-$d_6$, internal standard TMS) 9.40 (1H, brs), 7.46 (1H, d, J=8.3 Hz), 7.29~7.39 (5H, m), 5.03 (2H, s), 4.59 (2H, brs), 4.14 (1H, td, J=7.8, 11.7 Hz), 3.71~3.79 (1H, m), 3.46~3.54 (1H, m), 1.97~2.05 (1H, m), 1.83~1.94 (1H, m), 1.89 (3H, s), 1.70~1.80 (1H, m), 1.52~1.62 (1H, m). MS (ESI+) m/z: 391 [M+Na]$^+$.

(3S, P (S or R))-3-benzyloxycarbonylamino-1-amino(acetylamino)phosphinyl-2-piperidone $^1$H-NMR (DMSO-$d_6$, internal standard TMS) 9.41 (1H, brs), 7.48 (1H, d, J=8.8 Hz), 7.29~7.39 (5H, m), 5.03 (2H, s), 4.63 (2H, brs), 4.00~4.07 (1H, m), 3.52~3.63 (2H, m), 1.96~2.04 (1H, m), 1.90 (3H, s), 1.74~1.81 (2H, m), 1.61~1.72 (1H, m). MS (ESI+) m/z: 391 [M+Na]$^+$.

EXAMPLE 48

Synthesis of (3S, P (R or S))-3-amino-1-amino(acetylamino)phosphinyl-2-piperidone ½ fumarate Palladium black (45.0 mg) was added to a solution of (3S, P (S or R))-3-benzyloxycarbonylamino-1-amino(acetylamino)phosphinyl-2-piperidone (225.5 mg, 0.6122 mmol) in ethanol (15 mL), and the resulting mixture was stirred at room temperature for 4 hours under a hydrogen atmosphere.

The reaction mixture was filtered and the filtrate was concentrated under reduced pressure and then dissolved in a mixed solvent of water (2 mL) and ethanol (2 mL). Fumaric acid (35.5 mg, 0.3058 mmol) was added thereto and the resulting solution was concentrated, after which the crystals thus obtained were washed with ethanol to obtain the desired compound (141.4 mg, 79%).

$^1$H-NMR (D$_2$O, internal standard: 3-(trimethylsilyl)-propionic acid-2, 2, 3, 3-$d_4$ sodium salt) 6.54 (1H, s), 4.17 (1H, dd, J=12.2, 6.8 Hz), 3.82 (1H, tdd, J=5.4, 12.7, 7.7 Hz), 3.63~3.74 (1H, m), 2.40 (1H, td, J=12.2, 6.4 Hz), 1.92~2.15 (5H, m), 1.80 (1H, tdd, J=12.2, 9.3, 6.8 Hz). MS (ESI+) m/z: 257 [M+Na]$^+$.

EXAMPLE 49

Synthesis of (3S, P (S or R))-3-amino-1-amino(acetylamino)phosphinyl-2-piperidone ½ fumarate Palladium black (30.0 mg) was added to a solution of (3S, P (R or S))-3-benzyloxycarbonylamino-1-amino(acetylamino)phosphinyl-2-piperidone (150.5 mg, 0.4086 mmol) in ethanol (10 mL), and the resulting mixture was stirred at room temperature for 4 hours under a hydrogen atmosphere.

The reaction mixture was filtered and the filtrate was concentrated under reduced pressure and then dissolved in a mixed solvent of water (2 mL) and ethanol (2 mL). Fumaric acid (23.7 mg, 0.2042 mmol) was added thereto and the resulting solution was concentrated, after which the crystals thus obtained were washed with ethanol to obtain the desired compound (114.6 mg, 96%).

$^1$H-NMR (D$_2$O, internal standard 3-(trimethylsilyl)-propionic acid-2, 2, 3, 3-$d_4$ sodium salt) 6.53 (1H, s), 4.12 (1H, dd, J=11.7, 6.8 Hz), 3.70~3.77 (2H, m), 2.40 (1H, td, J=11.2, 4.9 Hz), 1.83~2.13 (6H, m). MS (ESI+) m/z: 257 [M+Na]$^+$.

EXAMPLE 50

Synthesis of (3S, P (SR))-3-benzyloxycarbonylamino-1-amino(n-butanoylamino)phosphinyl-2-piperidone At room temperature, butyric anhydride (0.31 mL, 1.8950 mmol) was added dropwise to a solution obtained by dissolving (3S)-3-benzyloxycarbonylamino-2-piperidone (520.5 mg, 1.5952 mmol) in pyridine (20 mL) with heating, and the resulting mixture was stirred at an external temperature of 60° C. for 2 days.

The reaction mixture was concentrated under reduced pressure and to the resulting residue was added a 30% aqueous acetone solution, followed by purification using Dianion HP-20 (20 mL; elution with a water-acetone gradient). The oil thus obtained was purified by the use of Dianion LH-20 (200 mL; methanol) to obtain the desired compound (300.3 mg, 47%).

$^1$H-NMR (CDCl$_3$, internal standard TMS) Stereoisomer A 7.85~7.93 (1H, m), 7.29~7.37 (5H, m), 5.65~5.72 (1H, m), 5.11 (2H, m), 4.21~4.31 (1H, m), 3.82~4.02 (3H, m), 3.67~3.75 (1H, m), 2.32~2.46 (1H, m), 2.26 (2H, t, J=7.3 Hz), 1.80~1.96 (2H, m), 1.52~1.66 (3H, m), 0.91 (3H, t, J=7.3 Hz). Stereoisomer B 7.74~7.84 (1H, m), 7.29~7.37 (5H, m), 5.57~5.65 (1H, m), 5.11 (2H, m), 4.21~4.31 (1H, m), 3.82~4.02 (3H, m), 3.56~3.66 (1H, m), 2.32~2.46 (1H, m), 2.26 (2H, t, J=7.3 Hz), 2.00~2.10 (1H, m), 1.80~1.96 (1H, m), 1.52~1.66 (3H, m), 0.91 (3H, t, J=7.3 Hz). MS (ESI+). m/z: 419 [M+Na]$^+$.

EXAMPLE 51

Synthesis of (3S, P (SR))-3-amino-1-amino(n-butanoylamino)phosphinyl-2-piperidone Palladium black (30.0 mg) was added to a solution of (3S, P (SR))-3-benzyloxycarbonylamino-1-amino(n-butanoylamino)phosphinyl-2-piperidone (153.2 mg, 0.3865 mmol) in ethanol (10 mL), and the resulting mixture was stirred at room temperature for 4 hours under a hydrogen atmosphere.

The reaction mixture was filtered and the filtrate was concentrated under reduced pressure to obtain the desired compound (101.1 mg, 100%).

$^1$H-NMR (CDCl$_3$, internal standard TMS) 3.87~3.95 (1H, m), 3.82 (2H, brs), 3.67~3.79 (1H, m), 3.43and3.40 (1H, dd, J=12.2, 6.8 Hz), 2.20~2.32 (3H, m), 1.53~2.09 (5H, m), 0.94and0.94 (3H, t, J=7.3 Hz) MS (ESI+) m/z: 285 [M+Na]$^+$.

EXAMPLE 52

Synthesis of (3S, P (SR))-3-benzyloxycarbonylamino-1-amino(t-butylacetylamino)phosphinyl-2-piperidone At room temperature, t-butylacetyl chloride (0.26 mL, 1.8716 mmol) was added dropwise to a solution obtained by dissolving (3S)-3-benzyloxycarbonylamino-2-piperidone (503.0 mg, 1.5416 mmol) in pyridine (20 mL) with heating, and the resulting mixture was stirred at the same temperature for 3 days.

The reaction mixture was concentrated under reduced pressure and to the resulting residue was added a 30% aqueous acetone solution, followed by purification using Dianion HP-20 (20 mL; elution with a water-acetone gradient). Then, the acetone was distilled off from the eluate under reduced pressure, followed by extraction with ethyl acetate. The ethyl acetate solution was washed with a saturated aqueous sodium chloride solution, dried over anhydrous sodium sulfate, and then concentrated. The oil thus obtained was crystallized from n-hexane to obtain the desired compound (624.7 mg, 95%).

$^1$H-NMR (DMSO-$d_6$, internal standard TMS) Stereoisomer A 9.28 (1H, brd, J=9.8 Hz), 7.41 (1H, brd, J=8.3 Hz), 7.29~7.38 (5H, m), 5.03 (2H, s), 4.57 (1H, brs), 4.56 (1H, brs), 4.14 (1H, td, J=7.8, 12.2 Hz), 3.77~3.84 (1H, m), 3.44~3.57 (1H, m), 1.97~2.07 (3H, m), 1.84~1.93 (1H, m), 1.72~1.81 (1H, m), 1.56 (1H, tt, J=12.2, 7.8 Hz), 0.94 (9H, s). Stereoisomer B 9.28 (1H, brd, J=9.8 Hz), 7.47 (1H, brd, J=8.8 Hz), 7.29~7.38 (5H, m), 5.03 (2H, s), 4.59 (1H, brs), 4.58 (1H, brs), 3.95~4.04 (1H, m), 3.61~3.68 (1H, m), 3.44~3.57 (1H, m), 1.97~2.07 (3H, m), 1.62~1.81 (3H, m), 0.94 (9H, s). MS (ESI+) m/z: 447 [M+Na]$^+$.

EXAMPLE 53

Synthesis of (3S, P (SR))-3-amino-1-amino(t-butylacetylamino)phosphinyl-2-piperidone Palladium black (50.0 mg) was added to a solution of (3S, P (SR))-3-benzyloxycarbonylamino-1-amino(t-butylacetylamino)phosphinyl-2-piperidone (261.7 mg, 0.6166 mmol) in ethanol (15 mL), and the resulting mixture was stirred at room temperature for 4 hours under a hydrogen atmosphere.

The reaction mixture was filtered and the filtrate was concentrated under reduced pressure to obtain the desired compound (175.5 mg, 98%).

$^1$H-NMR (DMSO-$d_6$, internal standard TMS) Stereoisomer A 9.28 (1H, brs), 4.54 (1H, brs), 4.54 (1H, brs), 3.70~3.80 (1H, m), 3.41~3.49 (1H, m), 3.31 (1H, dd, J=11.2, 6.8 Hz), 1.97~2.09 (3H, m), 1.62~1.92 (2H, m), 1.26~1.38 (1H, m), 0.94 (9H, s). Stereoisomer B 9.28 (1H, brs), 4.58 (1H, brs), 4.57 (1H, brs), 3.57~3.65 (1H, m), 3.49~3.57 (1H, m), 3.17 (1H, dd, J=11.2, 6.8 Hz), 1.97~2.09 (3H, m), 1.62~1.92 (2H, m), 1.38~1.47 (1H, m), 0.93 (9H, s). MS (ESI+) m/z: 313 [M+Na]$^+$.

EXAMPLE 54

Synthesis of (3S, P (SR))-3-benzyloxycarbonylamino-1-amino(cyclohexanecarbonylamino)phosphinyl-2-piperidone At room temperature, cyclohexanecarbonyl chloride (0.27 mL, 2.0183 mmol) was added dropwise to a solution obtained by dissolving (3S)-3-benzyloxycarbonylamino-2-piperidone (545.4 mg, 1.6715 mmol) in pyridine (20 mL) with heating, and the resulting mixture was stirred under ice-cooling for 3 hours and then at room temperature for 4 hours.

The reaction mixture was concentrated under reduced pressure and to the resulting residue was added a 30% aqueous acetone solution, followed by purification using Dianion HP-20 (20 mL; elution with a water-acetone gradient). Then, the acetone was distilled off from the eluate under reduced pressure, followed by extraction with ethyl acetate. The ethyl acetate solution was washed with a saturated aqueous sodium chloride solution, dried over anhydrous sodium sulfate, and then concentrated. The oil thus obtained was crystallized from ether-n-hexane to obtain the desired compound (555.2 mg, 69%).

$^1$H-NMR (DMSO-$d_6$, internal standard TMS) Stereoisomer A 9.23 (1H, brs), 7.42 (1H, d, J=8.3 Hz), 7.28~7.38 (5H, m), 5.02 (2H, s), 4.53~4.57 (2H, m), 4.11 (1H, td, J=7.8, 12.2 Hz), 3.73~3.82 (1H, m), 3.53~3.63 (1H, m), 2.14~2.23 (1H, m), 1.95~2.04 (1H, m), 1.47~1.92 (7H, m), 1.06~1.30 (6H, m). Stereoisomer B 9.23 (1H, brs), 7.46 (1H, d, J=8.3 Hz), 7.28~7.38 (5H, m), 5.02 (2H, s), 4.53~4.57 (2H, m), 3.94~4.02 (1H, m), 3.43~3.52 (2H, m), 2.14~2.23 (1H, m), 1.95~2.04 (1H, m), 1.47~1.92 (7H, m), 1.06~1.30 (6H, m). MS (ESI+) m/z: 459 [M+Na]$^+$.

EXAMPLE 55

Synthesis of (3S, P (SR))-3-amino-1-amino(cyclohexanecarbonylamino)phosphinyl-2-piperidone Palladium black (50.0 mg) was added to a solution of (3S, P (SR))-3-benzyloxycarbonylamino-1-amino(cyclohexanecarbonylamino)phosphinyl-2-piperidone (250.2 mg, 0.5733 mmol) in ethanol (6 mL), and the resulting mixture was stirred at room temperature for 16 hours under a hydrogen atmosphere.

The reaction mixture was filtered and the filtrate was concentrated under reduced pressure to obtain the desired compound (170.0 mg, 98%).

$^1$H-NMR (DMSO-$d_6$, internal standard TMS) Stereoisomer A 9.20 (1H, brs), 4.53 (1H, brs), 4.52 (1H, brs), 3.66~3.74 (1H, m), 3.41~3.49 (1H, m), 3.28 (1H, dd, J=11.2, 6.8 Hz), 2.15~2.25 (1H, m), 1.96~2.04 (1H, m), 1.55~1.89 (7H, m), 1.12~1.32 (6H, m). Stereoisomer B 9.20 (1H, brs), 4.55 (1H, brs), 4.54 (1H, brs), 3.51~3.61 (1H, m), 3.41~3.49 (1H, m), 3.16 (1H, dd, J=11.2, 6.8 Hz), 2.15~2.25 (1H, m), 1.96~2.04 (1H, m), 1.55~1.89 (7H, m), 1.12~1.32 (6H, m). MS (ESI+) m/z: 325 [M+Na]$^+$.

EXAMPLE 56

Synthesis of (3S, P (SR))-3-benzyloxycarbonylamino-1-amino(phenoxyacetylamino)phosphinyl-2-piperidone At room temperature, phenoxyacetyl chloride (0.32 mL, 2.3165 mmol) was added dropwise to a solution obtained by dissolving (3S)-3-benzyloxycarbonylamino-2-piperidone (504.0 mg, 1.5446 mmol) in pyridine (20 mL) with heating, and the resulting mixture was stirred at room temperature for 16 hours.

The reaction mixture was concentrated under reduced pressure and to the resulting residue was added a 30% aqueous acetone solution, followed by purification using Dianion HP-20 (20 mL; elution with a water-acetone gradient). Then, the acetone was distilled off from the eluate under reduced pressure, followed by extraction with ethyl acetate. The ethyl acetate solution was washed with a saturated aqueous sodium chloride solution, dried over anhydrous sodium sulfate, and then concentrated. The oil thus obtained was crystallized from ether-n-hexane to obtain the desired compound (421.2 mg, 67%).

$^1$H-NMR (DMSO-$d_6$, internal standard TMS) Stereoisomer A 9.57 (1H, brs), 7.52 (1H, d, J=8.3 Hz), 7.27~7.39 (7H, m), 6.95 (1H, t, J=7.3 Hz), 6.87 (2H, d, J=7.3 Hz), 5.03 (2H, s), 4.82 (1H, brs), 4.81 (1H, brs), 4.55 (2H, q, J=16.1 Hz), 4.14 (1H, td, J=7.8, 12.2 Hz), 3.72~3.80 (1H, m), 3.48~3.58 (1H, m), 1.96~2.06 (1H, m), 1.64~1.88 (2H, m), 1.56 (1H, tt, J12.2, 7.8 Hz) Stereoisomer B 9.57 (1H, brs), 7.53 (1H, d, J=8.3 Hz), 7.27~7.39 (7H, m), 6.95 (1H, t, J=7.3 Hz), 6.84 (2H, d, J=7.3 Hz), 5.04 (2H, s), 4.82 (1H, brs), 4.81 (1H, brs), 4.50~4.64 (2H, m), 3.98~4.07 (1H, m), 3.48~3.66 (2H, m), 1.96~2.06 (1H, m), 1.64~1.88 (3H, m). MS (ESI+) m/z: 483 [M+Na]$^+$.

EXAMPLE 57

Synthesis of (3S, P (SR))-3-amino-1-amino(phenoxyacetylamino)phosphinyl-2-piperidone Palladium black (40.0 mg) was added to a solution of (3S, P (SR))-3-benzyloxycarbonylamino-1-amino(phenoxyacetylamino)phosphinyl-2-piperidone (200.9 mg, 0.4363 mmol) in ethanol (6 mL), and the resulting mixture was stirred at room temperature for 16 hours under a hydrogen atmosphere.

The reaction mixture was filtered and the filtrate was concentrated under reduced pressure to obtain the desired compound (139.0 mg, 98%).

$^1$H-NMR (DMSO-d$_6$, internal standard TMS) 7.25~7.39 (2H, m), 6.95 (1H, t, J=7.3 Hz), 6.82~6.88 (2H, m), 4.76~4.84 (2H, m), 4.49~4.63 (2H, m), 3.16~3.80 (5H, m), 1.95~2.05 (1H, m), 1.62~1.88 (2H, m), 1.21~1.33and1.38~1.48 (1H, m). MS (ESI+) m/z: 349 [M+Na]$^+$.

EXAMPLE 58

Synthesis of (3S, P (SR))-3-benzyloxycarbonylamino-1-amino(cinnamoylamino)phosphinyl-2-piperidone At room temperature, cinnamoyl chloride (511.9 mg, 3.0726 mmol) was added to a solution obtained by dissolving (3S)-3-benzyloxycarbonylamino-2-piperidone (835.5 mg, 2.5606 mmol) in pyridine (33 mL) with heating, and the resulting mixture was stirred at room temperature for 18 hours.

The reaction mixture was concentrated under reduced pressure and to the resulting residue was added a 30% aqueous acetone solution, followed by purification using Dianion HP-20 (20 mL; elution with a water-acetone gradient). Then, the acetone was distilled off from the eluate under reduced pressure, followed by extraction with ethyl acetate. The ethyl acetate solution was washed with a saturated aqueous sodium chloride solution, dried over anhydrous sodium sulfate, and then concentrated. The oil thus obtained was crystallized from ether-n-hexane to obtain the desired compound (833.3 mg, 73%).

$^1$H-NMR (DMSO-d$_6$, internal standard TMS) Stereoisomer A 9.61 (1H, s), 7.57~7.60 (2H, m), 7.52 (1H, d, J=16.1 Hz), 7.41~7.48 (4H, m), 7.27~7.37 (5H, m), 6.72 (1H, d, J=16.1 Hz), 5.00 (2H, s), 4.72 (1H, brs), 4.72 (1H, brs), 4.18 (1H, td, J=7.8, 11.7 Hz), 3.82~3.90 (1H, m), 3.51~3.59 (1H, m), 1.54~2.07 (4H, m). Stereoisomer B 9.61 (1H, s), 7.57~7.60 (2H, m), 7.52 (1H, d, J=16.1 Hz), 7.41~7.48 (4H, m), 7.27~7.37 (5H, m), 6.72 (1H, d, J=16.1 Hz), 5.00 (2H, s), 4.75 (1H, brs), 4.75 (1H, brs), 4.03 (1H, q, J=6.8 Hz), 3.58~3.72 (2H, m), 1.54~2.07 (4H, m). MS (ESI+) m/z: 479 [M+Na]$^+$.

EXAMPLE 59

Synthesis of (3S, P (SR))-3-amino-1-amino(3-phenylpropanoylamino)phosphinyl-2-piperidone Palladium black (20.0 mg) was added to a solution of (3S, P (SR))-3-benzyloxycarbonylamino-1-amino(cinnamoylamino)phosphinyl-2-piperidone (201.0 mg, 0.4404 mmol) in ethanol (6 mL), and the resulting mixture was stirred at room temperature for 20 hours under a hydrogen atmosphere.

The reaction mixture was filtered and the filtrate was concentrated under reduced pressure to obtain the desired compound (140.5 mg, 98%).

$^1$H-NMR (CDCl$_3$, internal standard TMS) 7.15~7.34 (6H, m), 3.95 (2H, brs), 3.59~3.87 (2H, m), 3.28~3.38 (1H, m), 2.86~2.96 (2H, m), 2.58~2.68 (2H, m), 2.13~2.21 (1H, m), 1.71~2.02 (2H, m), 1.45~1.57 (1H, m). MS (ESI+) m/z: 347 [M+Na]$^+$.

EXAMPLE 60

Synthesis of (3S, P (RS))-3-benzyloxycarbonylamino-1-amino(4-methoxybenzoylamino)phosphinyl-2-piperidone At room temperature, 4-methoxybenzoyl chloride (377.7 mg, 2.4121 mmol) was added to a solution obtained by dissolving (3S)-3-benzyloxycarbonylamino-2-piperidone (602.0 mg, 1.8450 mmol) in pyridine (24 mL) with heating, and the resulting mixture was stirred at the same temperature for 6 hours.

The reaction mixture was concentrated under reduced pressure and to the resulting residue was added a 30% aqueous acetone solution, and the crystals were collected by filtration. Acetone was added to the crystals obtained and the insoluble material was filtered off, after which the filtrate was concentrated and the crystals thus obtained were washed with an ethyl acetate-ether mixed solvent to obtain the desired compound (220.1 mg, 26%).

$^1$H-NMR (DMSO-d$_6$, internal standard TMS) Stereoisomer A 9.49 (1H, brs), 7.89 (2H, d, J=8.8 Hz), 7.47 (1H, d, J=8.8 Hz), 7.27~7.37 (5H, m), 7.01 (2H, dd, J=8.8, 2.0 Hz), 4.99 (2H, s), 4.69~4.73 (2H, m), 4.12~4.20 (1H, m), 3.84~3.93 (1H, m), 3.82 (3H, s), 3.53~3.62 (1H, m), 1.50~2.07 (4H, m). Stereoisomer B 9.49 (1H, brs), 7.89 (2H, d, J=8.8 Hz), 7.43 (1H, d, J=8.8 Hz), 7.27~7.37 (5H, m), 7.01 (2H, dd, J=8.8, 2.0 Hz), 4.99 (2H, s), 4.69~4.73 (2H, m), 3.99~4.07 (1H, m), 3.81 (3H, s), 3.62~3.72 (2H, m), 1.50~2.07 (4H, m). MS (ESI+) m/z: 483 [M+Na]$^+$.

EXAMPLE 61

Synthesis of (3S, P (SR))-3-amino-1-amino(4-methoxybenzoylamino)phosphinyl-2-piperidone Palladium black (20.0 mg) was added to a solution of (3S, P (SR))-3-benzyloxycarbonylamino-1-amino(4-methoxybenzoylamino)phosphinyl-2-piperidone (112.5 mg, 0.2243 mmol) in ethanol (15 mL), and the resulting mixture was stirred at room temperature for 20 hours under a hydrogen atmosphere.

The reaction mixture was filtered and the filtrate was concentrated under reduced pressure to obtain the desired compound (79.0 mg, 99%).

¹H-NMR (CDCl₃, internal standard TMS) 7.84and7.83 (2H, d, J=8.8 Hz), 7.27~7.34 (1H, m), 6.87 (2H, dd, J=8.8, 2.0 Hz), 4.04~4.29 (2H, m), 3.70~4.03 (2H, m), 3.82and3.83 (3H, s), 3.35~3.43 (1H, m), 2.15~2.25 (1H, m), 1.77~2.11 (2H, m), 1.49~1.63 (1H, m). MS (ESI+) m/z: 349 [M+Na]⁺.

TEST EXAMPLE 1

Test for Evaluating Efficacy in Drug-Induced Leukopenia

The efficacy of the compound of Example 1 in drug-induced leukopenia was evaluated according to the method of Okabe et al. (Yakuri to Chiryo (Pharmacology and Treatment), Vol. 19, No. 6, p. 55, 1991).

ICR strain male mice (Crj:CD-1) aged 8 weeks were used in the test. The animals were divided into three groups of 3 or 4 animals each. On Day 0, cyclophosphamide was intraperitoneally administered once to all the groups in a dose of 200 mg/kg. From the next day, the following were intravenously and repeatedly administered to the groups, respectively, for 5 days (Days 1 to 5); a first group (a control group): physiological saline, a second group: the compound of Example 1 (30 mg/kg/day), and a third group: the compound of Example 1 (100 mg/kg/day). Blood was drawn from the orbital vein on Day 0 (before the administration of cyclophosphamide) and Days 2, 4, 6, 8 and 10, and the number of leukocytes was periodically measured to investigate the leukocyte-increasing effect of the compound of Example 1 on leukopenia induced by cyclophosphamide.

The results are shown in Table 1.

TABLE 1

Recovery of the number of leukocytes by the compound of Example 1 (unit: ×100/millimeter cube)

|  | First group (control group) | Second group | Third group |
| --- | --- | --- | --- |
| Day 0 | 60 ± 16.8 | 33 ± 7.8 | 81 ± 38.7 |
| Day 2 | 18 ± 6.6 | 23 ± 14.2 | 25 ± 8.3 |
| Day 4 | 9 ± 2.9 | 7 ± 1.8 | 13 ± 6.8 |
| Day 6 | 21 ± 2.5 | 25 ± 6.2 | 124 ± 144.2 |
| Day 8 | 71 ± 31.7 | 108 ± 52.8 | 139 ± 36.7 |
| Day 10 | 55 ± 11.3 | 58 ± 16.1 | 49 ± 7.3 |

That is, the numbers of leukocytes of the control group were 100, 30, 15, 35, 118 and 92% on Days 0, 2, 4, 6, 8 and 10, respectively; the numbers of leukocytes of the group treated with the compound of Example 1 (30 mg/kg/day) were 100, 70, 21, 76, 327 and 176% on Days 0, 2, 4, 6, 8 and 10, respectively; and the numbers of leukocytes of the group treated with the compound of Example 1 (100 mg/kg/day) were 100, 31, 16, 153, 172 and 60% on Days 0, 2, 4, 6, 8 and 10, respectively. This fact has made it clear that the recovery of the number of leukocytes to the initial value after the administration of cyclophosphamide requires 8 days in the case of the control group and that the recovery requires only 6 days, namely, the recovery is faster, in the case of the groups treated with the compound of Example 1. In addition, the data on Day 8 have proved that the compound of Example 1 is very effective in increasing the number of leukocytes.

TEST EXAMPLE 2

Test for Investigating the Increase of Leukocytes and the Decrease of Platelets in Normal Mice ICR strain male mice (Crj:CD-1) aged 8 weeks were used in the test. The animals were divided into 5 groups of 3 to 4 animals each. The following were intravenously and repeatedly administered to the groups, respectively, for 5 days; a first group: physiological saline as solvent, a second group: the compound of Example 45 (hydrochloride of the compound of Example 1) (10 mg/kg/day), a third group: the compound of Example 45 (50 mg/kg/day), a fourth group: the compound of Example 45 (250 mg/kg/day), and a fifth group: sulphostin (WO 99/25719 and JP-A-2000-327689; (3S, PR)-3-amino-1-amino(sulfoamino)phosphinyl-2-piperidone) (50 mg/kg/day). On the day subsequent to the last day in the administration period, blood was drawn from the abdominal aorta under anesthesia and the number of leukocytes and the number of platelets were measured. The results are shown in Table 2.

TABLE 2

Measurement of the number of leukocytes (unit: ×100/millimeter cube) and the number of platelets (unit: ×10000/millimeter cube) attained by the use of the compound of Example 45 and sulphostin

|  | Number of leukocytes | Number of platelets |
| --- | --- | --- |
| First group (control group) | 6 ± 1 | 78.4 ± 11.3 |
| Second group | 25 ± 13 | 76.0 ± 7.8 |
| Third group | 23 ± 19 | 84.9 ± 8.3 |
| Fourth group | 40 ± 18 | 81.1 ± 8.0 |
| Fifth group | 15 ± 5 | 57.1 ± 5.1 |

The compound of Example 45 increased the number of leukocytes to such an extent that the numbers of leukocytes of the groups treated with the compound of Example 45 were larger than that of the control group by the following factors; the 10 mg/kg/day group: 4.2, the 50 mg/kg/day group: 3.8, and the 250 mg/kg/day group: 6.7.

In addition, sulphostin decreased the number of platelets (73%) as compared with the control group, while the compound of Example 45 did not decrease the number of platelets in all the groups.

Thus, it has been proved that the α-amino-N-(diaminophosphinyl)lactam derivative of the present invention is very effective in increasing the number of leukocytes and hence is useful as a prophylactic or therapeutic agent for infectious diseases. Furthermore, it has become apparent that the α-amino-N-(diaminophosphinyl)lactam derivative of the present invention does not decrease the number of platelets and hence is excellent in harmlessness in its clinical employment.

TEST EXAMPLE 3

Measurement of Dipeptidyl Peptidase IV Activity

After 0.025 ml of 3.2 mM glycyl·prolyl·β-naphthylamide (BACHEM, Switzerland), 0.1 ml of 0.1 M Tris-maleic acid buffer (pH 7.2) and a drug were mixed, the final volume was adjusted to 0.2 ml with water. The resulting mixture was heated at 37° C. for 10 minutes, and 0.025 ml of a dipeptidyl peptidase IV solution partially purified from rat kidney homogenate by ammonium sulfate fractionation was added thereto, followed by incubation at 37° C. for 1 hour. After the incubation, the reaction was stopped by adding 0.1 ml of 0.5 M sodium citrate buffer (pH 3.78) containing 10% polyoxyethylene (20) sorbitan monourate and 0.2% Fast Garnet GBC salt (Sigma Chemical Co., U.S.A.), and absorbance (a) at 525 nm was measured. At the same time, a blank test was carried out without adding the sample to the buffer solution and absorbance (b) was measured. The dipeptidyl peptidase IV inhibition rate was calculated according to the calculation expression [(b−a)/b]×100. Table 3 shows the dipeptidyl peptidase IV 50% inhibition activity values of the compounds of the present invention measured by the method described above.

TABLE 3

Dipeptidyl peptidase IV 50% inhibition activity values (unit: microgram/milliliter) of the compounds of the present invention

| Compound No. | 50% inhibition activity value |
| --- | --- |
| Compound of Example 1 | 0.017 |
| Compound of Example 11 | 15 |
| Compound of Example 15 | 1.7 |
| Compound of Example 17 | 1.5 |
| Compound of Example 22 | 0.29 |
| Compound of Example 25 | 0.86 |
| Compound of Example 28 | 4.2 |
| Compound of Example 31 | 0.93 |
| Compound of Example 34 | 1.1 |
| Compound of Example 37 | 2.1 |
| Compound of Example 39 | 0.71 |
| Compound of Example 41 | 0.035 |
| Compound of Example 42 | 0.0093 |
| Compound of Example 43 | 0.022 |
| Compound of Example 44 | 0.0020 |
| Compound of Example 48 | 0.38 |
| Compound of Example 51 | 0.30 |
| Compound of Example 53 | 0.43 |
| Compound of Example 55 | 0.48 |
| Compound of Example 57 | 0.061 |
| Compound of Example 59 | 0.29 |
| Compound of Example 61 | 0.35 |

Thus, it has been proved that the α-amino-N-(diaminophosphinyl)lactam derivatives of the present invention have a powerful inhibitory effect on dipeptidyl peptidase IV and hence can be used as prophylactic or therapeutic agents for diseases in which dipeptidyl peptidase IV seems to participate, such as hormone modulators, immunomodurators, anti-inflammatories, antiallergics, antirheumatics, anti-HIV agents, therapeutic agents for type II diabetes, etc.

INDUSTRIAL APPLICABILITY

According to the present invention, there are provided novel α-amino-N-(diaminophosphinyl)lactam derivatives to be used as prophylactic or therapeutic agents for myelosuppression, therapeutic agents for infectious diseases and agents for increasing the number of leukocytes. In addition, according to the present invention, there are provided novel α-amino-N-(diaminophosphinyl)lactam derivatives having inhibitory effect on dipeptidyl peptidase IV. Furthermore, according to the present invention, there are provided drugs for mammal comprising the novel α-amino-N-(diaminophosphinyl)lactam derivative of the present invention which are effective against the symptoms described above and the like.

The invention claimed is:

1. An α-amino-N-(diaminophosphinyl)lactam compound represented by the following general formula (1), or a pharmacologically acceptable salt thereof:

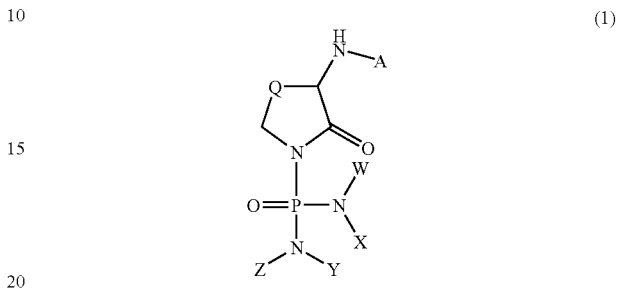

wherein A is a hydrogen atom, a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, an arylamino group, a heteroarylamino group, a lower acylamino group, a carboxyl group, a lower alkoxycarbonyl group, a carbamoyl group or a lower alkylaminocarbonyl group; W, X, Y and Z are independently a hydrogen atom, a lower alkyl group, an aryl group, a heteroaryl group, a lower alkenyl group, a cycloalkyl group, a lower acyl group, an arylacyl group, a heteroarylacyl group, a lower alkylaminocarbonyl group or an arylaminocarbonyl group, each of these groups being able to be substituted by a lower alkyl group, an aryl group, a heteroaryl group, a lower alkoxy group, an aryloxy group, a hydroxyl group, an amino group, a lower alkylamino group, a di-lower alkylamino group, a lower acylamino group, a carboxyl group, a lower alkoxycarbonyl group, a halogen atom, a cyano group, a nitro group, a carbamoyl group or a lower alkylaminocarbonyl group, or one or both of a combination of W and X and a combination of Y and Z form a cyclic group (s) through a saturated or unsaturated carbon-carbon bond or a saturated or unsaturated carbon-carbon bond containing 1 to 3 heteroatoms selected from nitrogen atom, oxygen atom and sulfur atom, said cyclic group (s) being able to be unsubstituted or substituted by a substituent (s) selected from the group consisting of lower alkyl groups, aryl groups, heteroaryl groups, halogen atoms, nitro group, cyano group, lower alkoxycarbonyl groups, carbamoyl group, lower alkylaminocarbonyl groups and carboxyl group, and W and X, or Y and Z, which do not form a ring, have the above-mentioned substituent; and Q is —(CH$_2$)$_n$— wherein n is 0 to 3.

2. An α-amino-N-(diaminophosphinyl)lactam compound or a pharmacologically acceptable salt thereof according to claim 1, wherein in general formula (1), A is a hydrogen atom or a lower alkyl group, said lower alkyl group being able to be substituted by an aryl group or a heteroaryl group.

3. An α-amino-N-(diaminophosphinyl)lactam compound or a pharmacologically acceptable salt thereof according to claim 1, wherein in general formula (1), A is a hydrogen atom; W, X, Y and Z are independently a hydrogen atom, a lower alkyl group, an aryl group, a lower acyl group, an arylacyl group, a lower alkylaminocarbonyl group or an arylaminocarbonyl group, each of these groups being able to be substituted by a lower alkyl group, an aryl group, a lower alkoxy group, an aryloxy group, a carboxyl group, a halogen atom, a cyano group, a nitro group, a carbamoyl group or a lower alkylaminocarbonyl group; and Q is —$(CH_2)_n$— wherein n is 0 to 3.

4. An α-amino-N-(diaminophosphinyl)lactam compound or a pharmacologically acceptable salt thereof according to claim 1, wherein in general formula (1), A is a hydrogen atom; W, X, Y and Z are independently a hydrogen atom, a lower alkyl group, a phenyl group, a 4-methoxyphenyl group, an acetyl group, a butanoyl group, a phenylacetyl group, a 3-phenylpropanoyl group, a phenoxyacetyl group, a t-butylacetyl group, a cyclohexanecarbonyl group, a cinnamoyl group, a benzoyl group, a 4-methoxybenzoyl group, a 4-nitrobenzoyl group, a 4-fluorobenzoyl group, a thenoyl group, an ethylaminocarbonyl group or a phenylaminocarbonyl group; and Q is —$(CH_2)_n$— wherein n is 0 to 3.

5. An α-amino-N-(diaminophosphinyl)lactam compound or a pharmacologically acceptable salt thereof according to claim 1, wherein in general formula (1), A is a hydrogen atom; W, X, Y and Z are independently a hydrogen atom, a lower alkyl group, a phenyl group, a 4-methoxyphenyl group, an acetyl group, a butanoyl group, a phenylacetyl group, a 3-phenylpropanoyl group, a phenoxyacetyl group, a t-butylacetyl group, a cyclohexanecarbonyl group, a cinnamoyl group, a benzoyl group, a 4-methoxybenzoyl group, a 4-nitrobenzoyl group, a 4-fluorobenzoyl group, a thenoyl group, an ethylaminocarbonyl group or a phenylaminocarbonyl group; and Q is —$(CH_2)_2$— (an ethylene group).

6. An α-amino-N-(diaminophosphinyl)lactam compound or a pharmacologically acceptable salt thereof according to claim 1, wherein in general formula (1), A is a hydrogen atom; all of W, X, Y and Z are hydrogen atoms; and Q is —$(CH_2)_n$— wherein n is 0 to 3.

7. An α-amino-N-(diaminophosphinyl)lactam compound or a pharmacologically acceptable salt thereof according to claim 1, wherein in general formula (1), A is a hydrogen atom; all of W, X, Y and Z are hydrogen atoms; and Q is —$(CH_2)_2$— (an ethylene group).

8. An α-amino-N-(diaminophosphinyl)lactam compound or a pharmacologically acceptable salt thereof according to claim 1, wherein in general formula (1), A is a hydrogen atom; all of W, X, Y and Z are hydrogen atoms; and Q is —$CH_2$— (a methylene group).

9. An α-amino-N-(diaminophosphinyl)lactam compound or a pharmacologically acceptable salt thereof according to claim 1, wherein in general formula (1), A is a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, a lower acylamino group, a carboxyl group, a carbamoyl group, a lower alkoxycarbonyl group or a lower alkylaminocarbonyl group; W, X, Y and Z are independently a hydrogen atom, a lower alkyl group, an aryl group, a cycloalkyl group, a lower acyl group, an arylacyl group, a heteroarylacyl group, a lower alkylaminocarbonyl group or an arylaminocarbonyl group, each of these groups being able to be substituted by a lower alkyl group, an aryl group, a heteroaryl group, a lower alkoxy group, an aryloxy group, a carboxyl group, a halogen atom, a cyano group, a nitro group, a carbamoyl group or a lower alkylaminocarbonyl group; and Q is —$(CH_2)_n$— wherein n is 0 to 3.

10. An α-amino-N-(diaminophosphinyl)lactam compound or a pharmacologically acceptable salt thereof according to claim 1, wherein in general formula (1), A is a lower alkyl group, an aryl group, a heteroaryl group, a lower alkenyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a di-lower alkylamino group, a lower acylamino group, a carboxyl group, a carbamoyl group, a lower alkoxycarbonyl group or a lower alkylaminocarbonyl group; all of W, X, Y and Z are hydrogen atoms; and Q is —$(CH_2)_n$— wherein n is 0 to 3.

11. An α-amino-N-(diaminophosphinyl)lactam compound or a pharmacologically acceptable salt thereof according to claim 1, wherein in general formula (1), A is a lower alkyl group or a cycloalkyl group, each of these groups being able to be substituted by a lower alkyl group, an aryl group, a heteroaryl group, a lower alkoxy group, a hydroxyl group, a halogen atom, an amino group, a lower alkylamino group, a lower acylamino group, a carboxyl group, a carbamoyl group, a lower alkoxycarbonyl group or a lower alkylaminocarbonyl group; all of W, X, Y and Z are hydrogen atoms; and Q is —$(CH_2)_n$— wherein n is 0 to 3.

12. An α-amino-N-(diaminophosphinyl)lactam compound or a pharmacologically acceptable salt thereof according to claim 1, wherein in general formula (1), A is a lower alkyl group or a cycloalkyl group, each of these groups being able to be substituted by an aryl group or a heteroaryl group; all of W, X, Y and Z are hydrogen atoms; and Q is —$(CH_2)_n$— wherein n is 0 to 3.

13. An α-amino-N-(diaminophosphinyl)lactam compound or a pharmacologically acceptable salt thereof according to claim 1, wherein in general formula (1), A is a methyl, ethyl, n-propyl, isopropyl or n-butyl group which may be substituted by a phenyl group or a 2-furyl group; all of W, X, Y and Z are hydrogen atoms; and Q is —$(CH_2)_n$— wherein n is 0 to 3.

14. An α-amino-N-(diaminophosphinyl)lactam compound or a pharmacologically acceptable salt thereof according to claim 1, wherein in general formula (1), A is a methyl, ethyl, n-propyl, isopropyl or n-butyl group which may be substituted by a phenyl group or a 2-furyl group; all of W, X, Y and Z are hydrogen atoms; and Q is —$(CH_2)_n$— wherein n is 1 or 2.

15. A pharmaceutical composition for treatment of leukopenia comprising a compound or a pharmacologically acceptable salt thereof according to claim 1 as an active ingredient.

16. A pharmaceutical composition for increasing the number of leukocytes comprising a compound or a pharmacologically acceptable salt thereof according to claim 1 as an active ingredient.

17. A method of inhibiting dipeptidyl peptidase IV in a patient, comprising administering to said patient a compound or a pharmacologically acceptable salt thereof according to claim 1 as an active ingredient.

\* \* \* \* \*